(12) United States Patent
Aeppli et al.

(10) Patent No.: US 9,347,884 B2
(45) Date of Patent: May 24, 2016

(54) MICROFLUIDIC DEVICE WITH DIRECT SAMPLE HEATING VIA ELECTROMAGNETIC RADIATION

(75) Inventors: Gabriel Aeppli, London (GB); Paul Dalby, London (GB); Matthieu Gaudet, Avelin (FR)

(73) Assignee: UCL BUSINESS PLC, London (GB)

( * ) Notice: Subject to any disclaimer, the term of this patent is extended or adjusted under 35 U.S.C. 154(b) by 0 days.

(21) Appl. No.: 13/379,945

(22) PCT Filed: Jun. 16, 2010

(86) PCT No.: PCT/GB2010/051001
§ 371 (c)(1),
(2), (4) Date: Mar. 9, 2012

(87) PCT Pub. No.: WO2010/149995
PCT Pub. Date: Dec. 29, 2010

(65) Prior Publication Data
US 2012/0152006 A1    Jun. 21, 2012

(30) Foreign Application Priority Data
Jun. 22, 2009 (GB) .................................. 0910759.0

(51) Int. Cl.
*G01N 21/00* (2006.01)
*G01N 21/64* (2006.01)
*B01L 3/00* (2006.01)
(Continued)

(52) U.S. Cl.
CPC ...... *G01N 21/6486* (2013.01); *B01L 3/502715* (2013.01); *B01L 7/52* (2013.01); *G01N 21/1717* (2013.01); *B01L 7/54* (2013.01); *B01L 2200/10* (2013.01); *B01L 2200/14* (2013.01); *B01L 2300/1861* (2013.01); *B01L 2300/1866* (2013.01); *B01L 2300/1872* (2013.01); *G01N 2021/1731* (2013.01)

(58) Field of Classification Search
USPC .......................... 356/246, 317, 320, 432–444
See application file for complete search history.

(56) References Cited

U.S. PATENT DOCUMENTS

| | | | |
|---|---|---|---|
| 7,058,244 B2 | 6/2006 | Iida et al. | |
| 2002/0197603 A1* | 12/2002 | Chow et al. | 435/6 |
| 2005/0164401 A1* | 7/2005 | Taguchi et al. | 436/174 |
| 2005/0202470 A1* | 9/2005 | Sundberg et al. | 435/6 |
| 2007/0026421 A1 | 2/2007 | Sundberg et al. | |

(Continued)

FOREIGN PATENT DOCUMENTS

| | | |
|---|---|---|
| WO | 96/41864 A1 | 12/1996 |
| WO | 03/037514 A2 | 5/2003 |

(Continued)

OTHER PUBLICATIONS

Baaske et al., "Melting curve analysis in a snapshot," Appl. Phys. Lett., 2007, vol. 91, 133901.

(Continued)

*Primary Examiner* — Tri T Ton
(74) *Attorney, Agent, or Firm* — Stites & Harbison, PLLC; Terry L. Wright; James R. Hayne

(57) ABSTRACT

A microfluidic device, for analysis, comprising: a chip (1) comprising a cavity (3); a light emitting diode or a laser which emits a first electromagnetic radiation (4) for heating a sample placed in the cavity in use; and an analytical assembly (7) configured to record a change in the sample arising from an interaction of the sample with the first source of electromagnetic radiation.

15 Claims, 17 Drawing Sheets

(51) Int. Cl.
   *B01L 7/00* (2006.01)
   *G01N 21/17* (2006.01)

(56) References Cited

U.S. PATENT DOCUMENTS

| | | | |
|---|---|---|---|
| 2008/0176289 A1* | 7/2008 | Zeng et al. | 435/91.2 |
| 2008/0248966 A1* | 10/2008 | Hansen et al. | 506/9 |
| 2009/0130745 A1 | 5/2009 | Williams et al. | |
| 2009/0234202 A1* | 9/2009 | Goix et al. | 600/301 |

FOREIGN PATENT DOCUMENTS

| | | |
|---|---|---|
| WO | 03/036302 A1 | 5/2006 |
| WO | 2007/051170 A2 | 5/2007 |

OTHER PUBLICATIONS

Duhr et al., "Thermophoresis of DNA determined by microfluidic fluorescence," Eur. Phys. J. E., 2004, vol. 15, pp. 277-286.

Hoffman et al., "Laser TemperatureJump Apparatus for Relaxation Studies in Electrolytic Solutions," Rev. Sci. Instrum., 1968, vol. 39:5, pp. 649-653.

Jaspe et al., "Do Protein Molecules Unfold in a Simple Shear Flow?," Biophysical Journal, Nov. 2006, vol. 91, pp. 3415-3424.

Schulze et al., Deep UV Laser-Induced Fluorescence Detection of Unlabeled Drugs and Proteins in Microchip Electrophoresis, Anal. Chem., 2005, vol. 77, pp. 1325-1329.

Slyadnev et al., "Photothermal Temperature Control of a Chemical Reaction on a Microchip Using an Infrared Diode Laser," Anal. Chem., 2001, vol. 73, pp. 4027-4044.

Eyring et al., "Fast Reactions in Solution," Annu. Phys. Chem., 1968, pp. 129-160.

Zhang et al., "DNA mutation detection with chip-based temperature gradient capillary electrophoresis using a slantwise radiative heating system," Lab Chip, The Royal Society of Chemistry, 2007, vol. 7, pp. 1162-1170.

\* cited by examiner

US 9,347,884 B2

MICROFLUIDIC DEVICE WITH DIRECT SAMPLE HEATING VIA ELECTROMAGNETIC RADIATION

FIELD

The invention relates to a microfluidic device, to methods of manufacture thereof and to the use of the device in a process for the detection of a signal. In particular, the invention relates to a micro fluidic device which provides for the heating of a sample and the recording of changes in the sample as a result of the heating process.

BACKGROUND

There exist in the art a wide range of techniques for probing molecules, these include techniques such as NMR, ESR, UV and IR spectroscopy in addition to crystallographic techniques, microscopy and electrochemical methods to name just a few.

Many devices can monitor and measure the changes in the structural conformation of molecules. This can be done using techniques which allow interaction to be observed and measured in response to perturbation by solvents, denaturants, temperature, pH or other interacting molecules. Such techniques allow the measurement of thermodynamic parameters such as stability, molecular affinity and associated rate constants for a wide range of molecules such as proteins, DNA, RNA and organic compounds. Perturbation by temperature is particularly useful for thermodynamic evaluations.

One such technique is the measurement of the intrinsic fluorescence of molecules. Fluorescence detection can be carried out using cuvette-based fluorometers or microtiter plate readers with typically 0.2-2 mL and 10-300 µL sample volumes respectively. The temperature of a single sample can be increased or decreased stepwise and the fluorescence measured when each temperature is equilibrated. For example, to determine the thermal stability of a protein or DNA, fluorescence must be measured across a range of typically 10-50 different temperatures in the range from 0 to 100° C. From this the transition mid-point (Tm) temperatures and enthalpy changes upon molecular denaturation can be determined.

The volumes of sample required for cuvette-based fluorometers and microtiter plate readers present two problems. The first is that they require a significant amount of an often limited source of sample. The second is that large volumes of sample take longer to equilibrate to new temperatures than smaller ones. This can be addressed to some degree by increasing the heat-transfer surface-area to volume ratios with a different (thinner) cuvette geometry though this also leads to a loss of fluorescence signal due to the decreased optical path length. However, the slow thermal equilibration times of the water baths, ovens or Peltier blocks used to incubate the sample cuvette or microtitre plate ultimately limits the throughput for measuring a range of increasing or decreasing temperatures to typically no better than 1° C. per minute.

More recently, micro fluidic devices have become available, these use significantly smaller sample volumes (of the order 0.1-10,000 nL) and therefore sample usage is reduced. They can also be devised with much higher heat-transfer surface-area to volume ratios to permit faster transfer of heat to the sample. However, the rate at which a range of temperatures can be sequentially measured at thermal equilibrium is still limited by the equilibration speed of the water baths, ovens or Peltier blocks in contact with the sample container.

One possible solution is the heating of the sample container via an electric current from wires that are in contact with the micro fluidic device surface (for example in WO 03/037514 and WO 03/036302). However, this method still has limitations in terms of the time taken for the wire to reach thermal equilibrium when the temperature is increased or decreased. In most experiments, the temperature of a sample in two or three dimensions is required to be homogeneous.

WO 03/037514 describes the use of two heating elements in contact with a microfluidic channel substrate. Heat transfer through the substrate to the sample in the channel creates a linear temperature gradient within the sample. Such heat transfer by thermal conductance through the substrate and diffusion through the sample requires a period of time for the sample to reach thermal equilibrium. Such a device cannot be used for rapid heating and cooling cycles as the cooling rate of the sample is limited by the cooling rate of the heating elements and local chip substrate. As used herein, with reference to the invention, the term chip is described the "active unit" of the microfluidic device; parallels can be drawn with microchips as the active units of computing devices, the chip of a micro fluidic device is the "active unit" where the sample is located and processed. In general the chip will comprise at least a cavity and means for supplying a sample to the cavity. The use of (electrical) thermal heating elements in WO 03/037514 would require the manufacture of micro fluidic chips with embedded heating elements to ensure good thermal contact. This increases the complexity and cost of manufacture for disposable sample chips.

WO 03/036302 also describes the use of two heating elements in contact with a micro fluidic channel substrate. However, WO 03/036302 additionally describes the use of multiple channels containing samples which flow in a direction from one heating element to another to create a thermal gradient. The thermal gradient can be used to alter the configuration of molecules and is monitored by UV fluorescence. This device has similar disadvantages to WO 03/037514, namely the need to manufacture microfluidic chips with embedded heating elements to ensure good thermal contact. The transfer of heat to the sample by conductance and diffusion is similarly slow, thus limiting the sample flow rate that can be achieved while still creating a thermal gradient across a useful range. Also, the sample cannot be cooled as rapidly as may be desired.

The systems of WO 03/037514 and WO 03/036302, like all of the above methods of sample heating, at all scales, are additionally limited by the need to transfer heat from the edges of the sample container to the centre of the sample; this occurs predominantly by thermal diffusion through the sample. A second disadvantage of these systems is the need to create a microfluidic channel with the heating element in thermal contact with the channel substrate. It is desirable for the micro fluidic chips containing the sample to be disposable due to rapid fouling of the channel by the sample materials. Therefore, the need to embed a thermal heating element within the disposable chip would lead to increased manufacturing complexity and costs.

The use of micro fluidic devices significantly reduces the sample volume and material quantity requirements. However, it would be advantageous to make use of these devices in the controlled rapid and localised heating of samples, to create thermal gradients within a sample, and to simultaneously measure the change in the sample as a result of the heating process at multiple points along the thermal gradient.

Electromagnetic heating of samples has been carried out in cuvette-based and larger sample devices ranging from temperature-jump instruments to domestic and industrial coffee makers. Hoffmann (H. Hofmann, E. Yeager, and J. Stuehr, 1968, Rev. Sci. Instrum., 39, 649) and Eyring (E. M. Eyring and B. C. Bennion, 1968, Ann. Rev. Phys. Chem., 19, 129) described the use of a Q-switched laser shining on a protein sample held, without flow, in a cuvette of 0.05 to 0.5 mm path length and 0.2-20 nL volume. An IR (infra red) laser beam was split to heat both sides of the cuvette evenly in order to create as uniform a thermal excitation as possible over the large probe volumes. A high intensity pulse of IR heating using high power IR lasers was found to raise the temperature of the entire sample very rapidly (ps to ms timescales) and by up to 40° C. Such systems have been used to monitor rapid events such as protein or DNA unfolding. However, such devices cannot be used to maintain a controlled temperature gradient along short microfluidic channels or to create a discrete series of sample plugs along a channel which have sequentially increased temperatures. Neither can they be used to obtain a constant sample temperature. Such gradients or incremental steps of temperature along a short microfluidic channel are required to enable complete equilibrium denaturation curves to be measured rapidly and within a single channel.

IR heating at a single site has also been applied to a liquid sample held between microscope slides (glass plates) and DNA denaturation induced with a temperature shift of up to 60° C. (from 30 to 90° C.) (Baaske et al, 2007, Appl Phys Lett 91, 133901). However, such a system does not permit rapid sample exchange such as is possible in a microfluidic channel. Also the temperature gradient achieved is difficult to control reproducibly in the glass plate system.

The use of UV (ultra violet) or blue lasers or UV-LEDs to induce sample fluorescence in microfluidics devices has also been described (Jaspe & Hagen, 2007 Biophys. J. 91:3415-3424; Schulze et al 2005 Anal. Chem. 77:1325-1329; Lee & Tripathi, 2007). Protein denaturation curves have also been obtained by mixing the protein with varying concentrations of chemical denaturants such as guanidine hydrochloride or urea (Jaspe & Hagen, 2007; Lee & Tripathi, 2007).

US 2005/0164401 describes the use of a light source to heat a sample on a microfluidic chip and to control the temperature of the sample. The technique applies the light source to a stationary sample or at a single position in a flowing sample. This technique cannot create a thermal gradient in a sample along the length of a microfluidic channel.

Accordingly, there is a need in the art to provide a micro fluidic device which overcomes or ameliorates some of the above problems.

SUMMARY

According to a first aspect of the invention there is provided a micro fluidic device, for analysis, comprising:
 a chip comprising a cavity;
 a first source of electromagnetic radiation for heating a sample placed in the cavity in use; and
an analytical assembly configured to record a change in the sample arising from an interaction of the sample with the first source of electromagnetic radiation.

The microfluidic devices of the invention have the benefits of analysis using a small sample volume and low total material requirements, but also use a technique for supplying heat that does not need to be in direct contact with the (potentially disposable) microfluidic channel substrate, and that enables the sample to be rapidly equilibrated at new temperatures during a series of either heating or cooling. For this reason the inventive device includes microfluidic chips that are simpler to manufacture than known chips for this application, and could allow measurements such as protein thermal denaturation curves and dissociation constants to be obtained more rapidly than by currently available methods.

The applicants have realised that this can be achieved, at least in part, by removing the dependence of the heating method on the thermal equilibration rate of the surrounding heating device, or the reliance on thermal diffusion rates into the sample from the walls of the sample container. For instance, direct and simultaneous heating throughout the sample material provides rapid temperature equilibration. The heating method can also be usefully localised such that selective regions of a sample can be locally heated to produce controlled and equilibrated thermal gradients within the sample. Current external heating methods such as water baths, and ovens cannot offer this precision of control, and currents passing through wire elements are limited by both the thickness of the wire element in contact with the sample container wall, and also by the diffusion of the heat in all directions into the sample.

The design of cheap and easy to manufacture microfluidic chips is hampered by the current complexity of design, in particular the need to incorporate heating apparatus. Overcoming the need to include this apparatus means that a chip can be provided which is inexpensive and simple to manufacture, as a result, the chips of the invention can be used disposably without loss of accuracy in sample detection and measurement. This ameliorates the problems associated with the high-throughput demands placed on microfluidic devices in which microfluidic channels can become readily fouled or blocked by the biological samples being tested.

It will generally be the case that the first source of electromagnetic radiation is an LED (light emitting diode) or laser. Where more than one source is present, a combination of LEDs and lasers may be used. It will also often be the case that the analytical assembly comprises a detector and a second source of electromagnetic radiation, wherein the second source of electromagnetic radiation interacts with the sample to produce a signal measurable by the detector. It may be the case that the analytical assembly does not comprise a second source of electromagnetic radiation.

The invention provides a device in which a thermal gradient can be quickly and easily created. Further, where the first source of electromagnetic radiation is an LED or laser, the application of heat can be switched on and off instantaneously such that the sample can cool rapidly without also requiring the cooling of elements in contact with the chip substrate. The use of such systems facilitates a near-instantaneous change in sample temperature (typically a change of 70° C. in less than 12 ms and across distances of over 100 µm). This rapid heating allows the device to be used with rapid sample flow through the cavity without compromising the ability to create a thermal gradient.

The use of rapid sample flow is desirable as not only is a high sample throughput obtained, but where the second source of electromagnetic radiation is of high energy, or has potential bleaching properties, damage or photobleaching of the sample can be avoided.

In some instances, the second source of electromagnetic radiation is selected from radio waves, microwaves, visible light, IR and ultraviolet radiation. Radio waves allow the detection of the signal by NMR, microwaves by ESR, visible light by techniques such as calorimetry, or IR or UV spectroscopy, IR radiation by techniques such as Fourier Transform IR (FTIR) spectroscopy or Raman spectroscopy, and UV radiation by techniques such as fluorometry or UV spectroscopy. It is particularly preferred that the second source of electromagnetic radiation is in the wavelength range 10 nm-500 nm (the UV and near visible part of the electromagnetic spectrum), as radiation of this wavelength is sufficiently high in energy that it will not interfere with the heating of the sample and will excite the molecules in the sample, but of sufficiently low energy that the molecules will not be damaged by the analytical process. In many examples, the second source of radiation will excite the molecules so that they luminesce, and it is envisaged that many embodiments of the invention will produce a photoluminescent signal, most typically a fluorescent signal.

In general, because of the requirement that the first source of electromagnetic radiation heats the sample, this is selected from visible, infra red and microwave radiation, which may be applied in the wavelength range 700 nm-10 cm (for example 700 nm-100 µm). IR radiation has been found to be most effective and of the wavelengths available, application of radiation in the wavelength range 1400-1600 nm has been found to directly excite the water molecules of the sample.

The use of IR focused into the sample allows faster heating of the samples than would be achieved using conventional methods. This is as a result of the direct and simultaneous heating of a volume of sample material without the need to wait for thermal conduction from a heat source applied through the sample container wall, or further thermal diffusion through the sample volume which eliminates the thermal equilibration time associated with the use of thermal or electrical heating elements and therefore allows the next equilibrium measurement to be obtained more quickly after the IR source is applied or changed in intensity.

Further, the use of a narrow beam width IR source, such as those from a laser, permits the localised heating of samples as the device can be configured such that only part of the sample is within the beam. Such narrowly focused application of heating is not possible using an external heat source applied to the sample container walls. Narrowly focused heating allows multiple sites within the same sample to establish equilibrium at different temperatures. These multiple sites can be discrete solution plugs in a channel, separated by gas, vacuum or oil to avoid thermal diffusion between the sample plugs. Alternatively heating multiple sites along the length of a single sample, or directing a radiation source in a parallel manner along the length of the sample, allows thermal gradients to be established rapidly and at equilibrium, for example along the length of a microfluidic channel. Either scenario allows the simultaneous measurement of the signal arising from these multiple sites to obtain a complete set of measurements of the sample at a range of temperatures much more quickly than using a stepwise change of sample temperature between each measurement. For instance, this multiple heating and multiple measurement array along the length of a microfluidic channel allows an entire thermal denaturation curve of a sample to be obtained simultaneously. Historically it was necessary to make use of much slower methods requiring measurement at each temperature sequentially.

In addition, the use of an IR LED/laser enables the heat source to be removed instantly by use of a shutter or by switching off the LED/laser. Therefore the sample can begin to cool immediately, either by thermal diffusion, radiation or by flowing the sample to a cooler region of the microfluidic device. The sample can therefore be subjected to rapid heating and cooling cycles. Other external heating methods (water-bath, oven, wire elements) would require mechanical removal of the heat source from thermal contact with the micro fluidic device to achieve a similar rapid removal of heating, as the heating devices themselves take time to lose heat when switched off. Such mechanical methods are expensive and more complex to implement in micro fluidic devices than simple switching of an IR LED/laser.

Use of a small volume of sample in a microfluidic scale device results in low power (e.g. 24 mW) infra-red lasers being sufficiently powerful to efficiently and rapidly heat the aqueous or other fluid samples by 0-100° C.

It will often be the case that the first and/or the second source of electromagnetic radiation is monochromatic as monochromatic radiation provides the greatest control over the response of the sample to the radiation. Further, it will often be the case that the second source of electromagnetic radiation will be a LED, a laser or a combination thereof; in many instances both the first and the second source of electromagnetic radiation will be a LED or a laser. Using a UV laser source is particularly preferred as these result in the detection of fluorescence with increased sensitivity.

The invention relates to devices including cavities; these may be any structure which can house the sample and can be of a wide variety of shapes including wells, channels, troughs and the like. The cavity will have one or more walls, the shape and number of the walls depending entirely upon the shape of the cavity. It is however important (particularly where the cavity is a closed structure), that at least a portion of the walls of the cavity allow the first and the second sources of electromagnetic radiation to pass through and interact with the sample. It is preferred that substantially all of the wall of the cavity allow the first and second sources of electromagnetic radiation to interact with the sample. It is equally important that the signal generated by this interaction can pass out from within the cavity for detection. As such, it is desirable that the walls are transparent or translucent to radiation at the wavelengths used and generated. It is preferred that the transmittance of the walls to the first and/or the second source of electromagnetic radiation and/or the signal is in the range 50-99.9%, often 80-99.9%, in most examples, 95-99.9%.

Often the cavity will be a channel, as the elongate nature of a channel facilitates the simultaneous measurement of the effect of heating the sample at different points along the channel. As used herein, the term "channel" is intended to mean an open groove(s) in the chip, and closed pipe-like structures. Accordingly, the term "channel" includes within its scope capillary tubing. In many examples the cross-sectional dimensions of the channel will be in the range of 1-150 µm (channel width)×1-150 µm (channel depth), often 10-100 µm (channel width)×10-100 µm (channel depth), so that the fluid to be analysed may be passed through the channel.

The invention permits the heating along a length of microfluidic channel using a first source of electromagnetic radiation, such as a LED or laser, to create a thermal gradient along that length, with simultaneous measurement of the resulting signal (such as fluorescence) along the same channel length being heated. As used herein the term "simultaneous" is intended to refer to two events which occur at the same time, or substantially at the same time, in that for the bulk of the time (80-100%, often 90 or 95-100%) during which the two or more events are occurring, they will both be in operation.

As noted above, the measurement may use a second laser or LED, which would in most instances produce UV or blue light, also focused on the cavity at or close to the point at which the sample is heated by the first source of electromagnetic radiation. In many cases, the interaction of the UV or blue LED/laser with the sample will result in a fluorescence emission signal which can then be recorded using a detector such as a CCD camera, photomultiplier tube, or photodiode.

Typically, microfluidic devices are used with flowing samples; however, the samples utilised in the invention may be static or flowing. Where a flowing sample is used this will flow at a speed in the range 0.1-150 µl min$^{-1}$, often 0.5-100 µl min$^{-1}$, or 1-50 µl min$^{-1}$, or even 5-20 µl min$^{-1}$. Such flow rates are considered to be rapid and are desirable to allow analysis of unstable or rapidly changing systems. Rapid flow rates also provide a high sample throughput.

The design of cheap and easy to manufacture microfluidic chips that can be used to pass radiation sources into microfluidic samples is hampered by the difficulty in correctly aligning and spacing the laser radiation sources along the microfluidic channel. For this reason, the devices of the invention will often comprise at least one waveguide. Where present, the waveguides will be positioned on the chip and sometimes in other areas of the device. As used herein the term "waveguide" is intended to include optical fibres, lenses and optical waveguides; often optical fibres will be used.

Providing a chip with the correct alignment for the two sources of electromagnetic radiation would mean that a chip as described herein could be much simpler than known chips, since the need to include components other than the microfluidic channel and the waveguides is removed. Such chips would be sufficiently inexpensive that they could be used disposably without loss of accuracy in sample detection and measurement.

The waveguides may be used in a variety of combinations, singularly and in arrays. For instance, the device of the invention may be configured so that the first and the second source of electromagnetic radiation pass through the same waveguide or adjacent waveguides. As used herein, the term "adjacent" is intended to mean directly side by side, or separated only by a small gap without any significant structural features in-between. A typical gap would be in the region of 10-150 µm, often 25-100 µm, in some examples 50-100 µm or 50-75 µm.

The use of the same or adjacent waveguides for the first and second source of electromagnetic radiation (i.e. for the heating and analytical functions) greatly simplifies the manufacture of the device. In particular, where the same waveguide is used, fewer waveguides are needed. As such, the waveguides are preferably fabricated from a material that transmits both radiation sources simultaneously.

It can be advantageous, where the cavity is a channel, and the sample is a flow sample, for the first source of electromagnetic radiation to pass through a first waveguide and the second source of electromagnetic radiation to pass through a second waveguide adjacent to the first waveguide in a position downstream of the first waveguide. This allows analysis of the effect of the heating from the first source of electromagnetic radiation, directly after heating as the affected molecules pass beyond the zone of sample heating. As such, in some illustrations of the invention, the array of waveguides may comprise an alternating sequence of first waveguides through which the first source of electromagnetic radiation passes, and second waveguides through which the second source of electromagnetic radiation passes.

In many examples the waveguides will be present in arrays along the side of the channel, often alternating as described above. It could therefore be the case that in some embodiments each of the multiple sources of the first source of electromagnetic radiation is passed through one of an array of waveguides placed around the cavity. By around the cavity it is meant that the waveguides are positioned so as to focus the first source of electromagnetic radiation onto specific points of the cavity.

Whether or not the waveguides are present, the placing of the first source of electromagnetic radiation at multiple points along the length of a flowing microfluidic sample allows the creation of a thermal gradient in the sample along the length of the channel. As such, it will often be the case that the first source of electromagnetic radiation comprises multiple sources of radiation. Each of these may be directed at a different region of the sample in the cavity and may each be at different frequencies or of different power outputs. The reason that the first source of radiation will often be at different frequencies or power outputs along the length of the channel (whether or not waveguides are present), is to generate the temperature gradient. At the hotter point of the gradient, the frequency may be higher or the power greater to heat the sample more than further down the gradient. In most cases, variations in the power output will be used to create the temperature gradient. As noted above, this arrangement allows samples to be rapidly measured for multiple temperatures simultaneously.

An array of such waveguides placed along the length of a channel can therefore direct the first source of electromagnetic radiation to multiple regions of the sample in the channel. This allows localised temperature differences to be established in a single continuous sample, or in individual plugs of sample distributed along the channel. Using the same or similar distribution of waveguides along the same length of the channel to apply the second source of electromagnetic radiation enables the simultaneous fluorescence (or other characteristics) of molecules to be determined for a sample equilibrated at multiple temperatures along the length of the channel. The sample may or may not be flowing through the channel.

Often the temperature gradient will be arranged in flowing samples such that the highest temperatures are observed at or near to the sample inlet. However, some examples may show a reversed gradient where the sample flows through the device from cooler to warmer regions before exiting the device.

The highest wavelength used for the first or the second source of electromagnetic radiation (often around 1600 nm, 1550 nm is often used for the first source of electromagnetic radiation) determines the minimum spacing of the waveguide(s), this is potentially only a few microns.

Alternatively, the first and second sources of radiation, and hence the waveguides (where present) associated with these may be arranged independently such that the first source of radiation simply creates a temperature gradient, and the second source or sources of radiation monitor the effect of the temperature on the sample. As such, it will often be the case that the second source of electromagnetic radiation comprises multiple sources of radiation. Each of these may be directed at a different region of the sample in the cavity so as to produce a response in the sample when under different temperature conditions. In addition, whether directed to parts of the sample at the same or different temperatures, the multiple sources of the second source of electromagnetic radiation may be at different frequencies or of different power outputs. Different frequencies, for instance, may cause different forms of excitation within the sample, resulting in multiple signals from a single experiment. This may be of particular use where the sample is not being processed through a temperature gradient, but heated uniformly throughout the sample. Alternatively, each of the multiple sources of the second source of electromagnetic radiation may be at the same frequency and/or power output.

Waveguides may also be present to gather the signal produced by the first source of electromagnetic radiation, for instance if there is no second source of electromagnetic radiation because the signal constitutes radiation emitted from the sample as a result of the heating. This may be IR radiation being emitted at a wavelength or amplitude different from the wavelength or amplitude of the first source of electromagnetic radiation. Alternatively, waveguides may be present to gather the signal produced by the interaction of the first and/or second source of electromagnetic radiation with the sample, such as fluorescence emission, or the signal resulting from a change in nuclear or electron spin. As such, the microfluidic device of the invention may comprise waveguides through which this signal passes. As with the waveguides described above, the waveguides associated with the signal path may be a single waveguide, or multiple waveguides arranged in an array.

As such, there is envisioned a device wherein the waveguide(s) through which the signal passes are arranged relative to, and preferably aligned with, the waveguide(s) through which the first or, in most cases, the second source of electromagnetic radiation passes such that the signal produced by the interaction of each of the multiple sources of the second source of electromagnetic radiation with the sample pass through a waveguide to the detector. The deliberate arrangement of the signal waveguides relative to the source waveguides is advantageous as it maximises the collection of the signal generated.

In some embodiments, there will be two or three waveguides. These embodiments may comprise a first waveguide through which the first and (where present) the second source of electromagnetic radiation passes and a second waveguide through which the signal passes. Alternatively, a first waveguide may be present through which the first source of electromagnetic radiation passes, a second waveguide through which the second source of electromagnetic radiation passes and a third waveguide through which the signal passes. These embodiments may form the basis for an array of repeating units of the types described above, or may be used as simple groupings of two or three waveguides.

It may be that, for embodiments where the cavity is a channel and wherein the multiple sources of the first source of electromagnetic radiation and/or the multiple sources of the second source of electromagnetic radiation are arranged in an array, that these are arranged so that the radiation meets a wall of the channel at an angle in the range 30°-150° relative to the longitudinal axis of the channel. This angle may also be in the range 80°-100° relative to the longitudinal axis of the channel, or even substantially perpendicular (i.e. at around 90°).

In a particular design of the microfluidic chip, where the cavity is a channel, combed waveguides perpendicular to each sides of the channel, may be used to enable multiple points of excitation from both the first and the second sources of electromagnetic radiation (for instance, IR thermal excitation and UV fluorescence excitation). The excitation is designed to occur along a length of the channel. Such a system enables a thermal transition of the sample to be measured from data collected along the length of the channel, as each point of thermal excitation increases the sample temperature incrementally to create a thermal gradient.

In an alternative embodiment to that described above, the first source of electromagnetic radiation may comprise a single source of radiation. Where this is the case, the first source of electromagnetic radiation will typically be directed along the length of the sample in the channel thus creating a thermal gradient in the sample along the length of the channel. This method has the advantage that it requires only a single source of radiation to create a thermal gradient along the length of illuminated sample in the channel, thus the construction of devices according to this embodiment is very simple.

Often the single source of radiation is arranged substantially parallel to a direction of flow of a flowing sample. However, this is not essential in order to create the gradient and angles in the range ±20°, ±15°, ±10°, ±5° could also be applied to the system. As used herein the term "single source" is intended to mean radiation originating from a single point of origin, rather than limiting the invention to a single radiation emitting unit. As such, in this embodiment the single source may be, for instance, a single LED/laser or a cluster of LEDs, lasers or a combination thereof, grouped together so that the radiation emitted from them appears to come from a single region of the device, as opposed to the embodiment above where the multiple sources of the first source of electromagnetic radiation clearly originate from different points around the cavity.

In this embodiment, the second source of electromagnetic radiation and any waveguides associated with this will be arranged for interaction with the sample much as described above and independently of the first source of radiation.

Thus far, the invention has been cast in terms of a first source of electromagnetic radiation, optionally in combination with a second source of electromagnetic radiation. It should be understood, however, that third, fourth or even more sources of radiation may be present, the physical constrictions of the device allowing. The presence of multiple sources of radiation, operating at different wavelengths, would allow the study of multiple facets of the sample molecules using a single device. Such study could be simultaneous, or in many instances merely offer a single device suitable for multiple applications, in which not every source will be applied to every sample, but which offers a single disposable device to the user.

The device may additionally comprise a motherboard. As used herein the term "motherboard" is intended to be analogous with the use in computing terms in that the motherboard houses the chip/active unit of the device. The presence of the motherboard provides a novel two component motherboard/reagent chip design facilitating accurate alignment of the sources of electromagnetic radiation to the correct spacing of waveguides placed adjacent to a cavity. It will often be the case that where the motherboard is present, the chip will be housed within the motherboard. This design means that the chip can be disposable and cheaper to manufacture, as there is no need for it to contain the more complex elements of microfluidic devices, such as the pumping apparatus and the sources of electromagnetic radiation. A further advantage is that the chip can be easily exchanged when the reagents foul or block the micro fluidic channels as direct contact of the heating mechanism with the chip is not required. Further, unlike prior art devices, the inventive device does not require a heating element to be in thermal contact with the microfluidic channel substrate containing the sample. Accordingly, there is optionally provided a device in which the chip is interchangeable within the device.

The motherboard will often comprise one or more of: fluid connectors for introducing the sample to the cavity on the chip, fluid pumps and waveguides.

Where the chip is removable from the motherboard, it will often be the case that a compliant layer of material will be positioned between the chip and the motherboard. This layer ensures a secure seal between the fluid pumping system on the motherboard and the chip such that the sample will be pumped into the cavity on the chip without loss of sample. The compliant material will often be a compliant plastics material such as a rubber or a gel.

It is generally preferable that the motherboard include one or more waveguides which are aligned with waveguides on the chip, so that simple placement of the chip in the housing of the motherboard will provide a device in which the sources of electromagnetic radiation and the detector are pre-aligned with the waveguides on the chip. The presence of this feature provides for a device which is quick and simple to operate. In order to achieve this, the motherboard often comprises an optical component and a fluidic component, the optical component often forming the upper surface of the device, with the fluidic component below.

The device can be developed in various ways. To meet the requirement for the necessity of low cost fabrication of this kind of chip, polymers are likely to be used as a basic material. A wide variety of polymers may be used for the substrate fabrication, either alone or in combination as would be known to the person skilled in the art. However, a PMMA (Poly methyl methacrylate), PDMS (Polydimethylsiloxane), glass or silicone substrate is particularly preferred, most often PDMS. The wall of the cavity and the waveguide are often fabricated on a layer of photoresist in one step of photolithograph and in preferred examples a layer of resist deposited on a PMMA cover is thermally bonded under pressure with the rest of the device. The cavity can be designed for flow samples by the provision of two drill holes in the substrate to provide access to the cavity. Upchurch™ Nanoports are often used to link the junctions created by the drill holes to the pumping system.

In one embodiment of the invention, a device is described with integrated optical measurement of fluorescence integrated with localised temperature control. Heating of a localised region of a channel is achieved using an IR laser distributed at multiple points along a short length of the channel, or alternatively transmitted along the length of the sample channel. Fluorescence measurements can be made using a second laser or other radiation source and the emission of fluorescence from samples (especially proteins, DNA, viruses and cells) is detected using a photomultiplier tube, photodiode, or photo detector including e.g. CCD arrays. Both lasers can be directed to the channel either directly or through the use of waveguides integrated onto the microfluidic chip.

According to a second aspect of the invention there is provided a process for the detection of a signal from a sample, comprising placing the sample into a microfluidic device as defined in the first aspect of the invention; and recording a change in the sample. In this process, the sample may comprise solution plugs in a cavity which is a channel or a single sample flowing through the cavity.

The general operation of micro fluidic devices will be well known to the person skilled in the art; however, the device of the invention may optionally be used in the following particular ways.

Often a property selected from: a thermal gradient in the sample, an amplitude of a thermal gradient in the sample, and an absolute temperature in the sample; will be modulated in the process by altering the flow rate of the sample through the cavity in a flowing sample, or by moderating the power of the first source of electromagnetic radiation in a flowing or a static sample. Similarly, a shape of a thermal gradient in the sample may be modulated by altering the relative power of one or more of multiple first sources of electromagnetic radiation positioned adjacent to different points of the cavity. Such modulation allows simple modification of the conditions applied to the sample, and flexibility of experiment.

It will also often be the case that as part of the process of the invention, the device used in the process has been calibrated using thermally sensitive calibration materials. The materials may be thermally sensitive fluorescent or luminescent chemicals such as TAMRA (carboxytetramethylrhodamine), BCECF (2'-7'-bis(carboxyethyl)-5(6)-carboxyfluorescein), GFP (green fluorescent protein) derivatives, or thermo-luminescent materials or liquids, and will be placed in the same manner as a sample, within the device to calibrate the thermal gradients produced by the IR heating. This eliminates the need for an independent measurement of temperature, such as a thermocouple or other device to be manufactured as part of the micro fluidic chip or motherboard. It can also take advantage of the same detector used in the device to detect the signal, although a separate detector, for instance a confocal microscope system, may also be used. The detector associated with the device can be used to determine the temperature related to, for instance, the fluorescence or luminescence of the calibration molecules or materials, at different points within in the cavity.

Accordingly, calibration may occur prior to use of the device. It may also occur substantially simultaneously with the recording of a change in the sample, in instances where the calibration chemicals will not interact with the sample molecules to give false results. Simultaneous calibration is advantageous as it removes a step of the analytical process; however, many samples will be sensitive to the presence of the calibration chemicals and accordingly, calibration as a separate and discrete step in the process is advantageous as it allows the device to be used with a wide variety of samples.

In some embodiments, such as those described above, a stable temperature gradient is set up in the device, and this is applied to the sample. In other embodiments, a uniform temperature is applied to the whole sample. In further embodiments, the sample is alternately heated and cooled by moderating the power of the first source of electromagnetic radiation applied to the sample. The heating and cooling may be of a particular sample or it may be of the system as a whole, for instance, to allow a sample already tested to flow from the cavity and fresh sample to enter the cavity and equilibrate for testing. Such techniques allow rapid repetition of the sample analysis.

As used herein the term "recording" is intended to mean the gathering of the data associated with the change and does not require that the data be actively observed or stored, although the data will in most instances not only be stored but also later observed and analysed whether by a human or computing device.

Accordingly, the electromagnetic radiation may be applied to the sample using continuous wave or pulsing techniques. As such, the recording of a change in the sample by the detector may use a method selected from continuous wave, or pulsing techniques. Often, as described above, both the first and the second source of electromagnetic radiation are pulsed.

Further, the signal obtained from the sample may be processed using techniques well known to the skilled person. The signal processing steps may consist of a mathematical high frequency filter and a ratio to a reference measurement, which reduces the level of noise relative to the required signal.

A further advantage of the chip of the invention is ease of cleaning of the cavity in the event that the chip is not being used disposably. In some embodiments of the process a cleaning solution (such as a detergent, complexing agent, alkali or acid) may be used to flush the cavity, air flushes can also be used to dry the cavity before reuse. In some examples, water or a buffer solution may be flushed through the cavity after cleaning, and fluorescent measurements taken in the absence of sample to ensure that all of the sample has been removed from the cavity. Often a buffer solution will be used. In embodiments where the device is a flow device, cleaning may occur as part of a continuous flow process. For instance, the sample could be passed through the cavity, followed by a bubble of air to prevent contamination of the sample by cleaning solution which follows the sample through the cavity.

Optionally, a further air bubble may be passed through the cavity, this may be followed by water or a buffer solution, which is in turn possibly followed by a further air bubble before the next sample is passed into the cavity. The skilled person would appreciate that whilst advantageous to dry the cavity and prevent mixing of the solutions flowing through the cavity, the air bubbles are not essential to the cleaning process. In addition, the bubbles may be a gas other than air, such as oxygen, nitrogen, argon or mixtures thereof. Similarly the use of water or a non-sample containing buffer solution is optional.

In a third aspect of the invention there is provided a method for the manufacture of a device according to the first aspect of the invention comprising providing a chip with a cavity, housing the chip within a motherboard and supplying an analytical assembly configured to record a change in a sample in the cavity in use. This method may comprise the additional step of providing waveguides in the motherboard and the chip which are aligned. Such fabrication techniques would be well known to the person skilled in the art.

It will be appreciated that whilst the discussion of the invention has been primarily related to the detection of a signal induced by a first or second source of electromagnetic radiation, the device of the invention may incorporate other analytical apparatus, or be used with other analytical apparatus. For instance, the analytical apparatus may be apparatus for SPR assays or micromechanical bending, for interactions with surface-immobilised targets. In some examples the device may be a flow device and the sample may be passed, for instance, through a cantilever assay array before being passed into the device for analysis using detection means such as fluorescence detection.

There are a wide variety of possible applications for the device of the invention, these include high-throughput and small (0.1 pL to 10 μL) applications for measurement of:

Protein stability and denaturation: As the temperature of the solution increases, protein complexes dissociate and native proteins denature causing changes in the intrinsic fluorescence signal. The temperature at which this occurs measures the conformational stability of the protein or protein complex. Such measurement can therefore be used to analyze protein complexes such as viral capsids.

For instance, the device of the invention enables thermally induced changes to be measured rapidly for small volumes of biological and non-biological samples. For example, if a laser emitting a 266-295 nm wavelength is used in combination with a capillary fibre linked to a pumping system and detection of fluorescence emission with a photomultiplier tube, the intrinsic fluorescence of proteins containing tryptophan, tyrosine and phenylalanine residues can be measured. Such measurements of protein fluorescence (without IR heating) in capillaries have been described previously. A diffraction grating or optical filter can be used to reduce the signal reaching the detector at wavelengths preferably below 300 nm. Changes in protein structure and conformation as measured by intrinsic fluorescence are stimulated using an IR laser of a wavelength which can produce thermal excitation of water molecules in the sample (ideally 1498 nm). Measurement of the intrinsic fluorescence during thermal excitation enables the melting temperature (Tm) of the protein to be determined. This temperature is a direct measure of the stability of the protein and can be used to determine the effect of additives, bound ligands or drugs, or protein mutations upon the global protein stability. The temperature increase in the sample can be regulated by variation of the laser power and by the flow rate of the sample through the microfluidic device, or by the spacing of the points along the cavity at which the IR laser is introduced.

Protein conformation, folding and unfolding: As the temperature of the solution increases, protein complexes dissociate and native proteins denature causing changes in the intrinsic fluorescence signal. The signal amplitude difference between the native and denatured states can be used to measure the extent of native protein in a sample relative to a standard fully native protein sample. Also, changes in the shape and number of transitions indicate changes in protein unfolding pathways or the appearance of new protein conformational states such as misfolded protein.

Protein aggregation: When proteins aggregate there is typically an associated change in the apparent intrinsic fluorescence signal. Furthermore, the appearance of less sigmoidal transitions also indicates a loss of unfolding cooperativity typical of aggregation events.

Protein concentration: Intrinsic protein fluorescence provides a sensitive measure of protein concentration when compared to a known standard sample. This method can also be used to determine the concentration of protein-based viral particles in solution.

Control of temperature in microfluidic channels enables polymerase chain reaction (PCR) for amplification of DNA and RNA: Fluorescence measurement can be used to determine the quantity of nucleic acid products formed. The sample could be subjected to one or more cycles of various temperatures suitable for performing PCR. The temperatures could be controlled and altered by changing the IR laser power and/or the fluid flow rate through the channel. An example PCR temperature cycle (i-iii) consists of:

i) 94-98° C. to denature the sample DNA or RNA strands;
ii) 40-72° C. to re-anneal DNA or RNA strands; and
iii) 65-75° C. for the DNA or RNA polymerisation reaction to occur.

Cycles can be repeated until the desired DNA amplification or RNA reverse transcription is achieved.

DNA sequencing reactions employ PCR to produce fragments incorporating fluorescent dye termination bases: The devices described could be used to control the PCR reaction, as above, for this application.

Time-resolved fluorescence intensity: The application of rapid laser pulses to protein samples can be used to obtain fluorescence decay measurements of protein samples in solution. The rate of decay is a function of protein size and sample viscosity and so this device can be used to measure them at various temperatures.

Chemical Reaction Vessels: The microfluidic devices of the invention could further be used as chemical reaction vessels, in such embodiments the analytical assembly would be optional, although it may be present to allow real time monitoring of the reactions' progress. There is therefore provided in a further aspect of the invention a process for heating a micro fluidic chip using a first source of electromagnetic radiation. As noted above, the electromagnetic radiation will typically be IR radiation and will typically be emitted from an LED and/or laser.

Unless otherwise stated each of the integers described in the invention may be used in combination with any other integer as would be understood by the person skilled in the art. Further, although all aspects of the invention preferably "comprise" the features described in relation to that aspect, it is specifically envisaged that they may "consist" or "consist essentially" of those features.

Unless otherwise stated, all numerical values appearing in this application are to be understood as being modified by the term "about".

FIGURES

The invention will now be described, by way of example only, by reference to the accompanying drawings, of which:

Figure 21A:
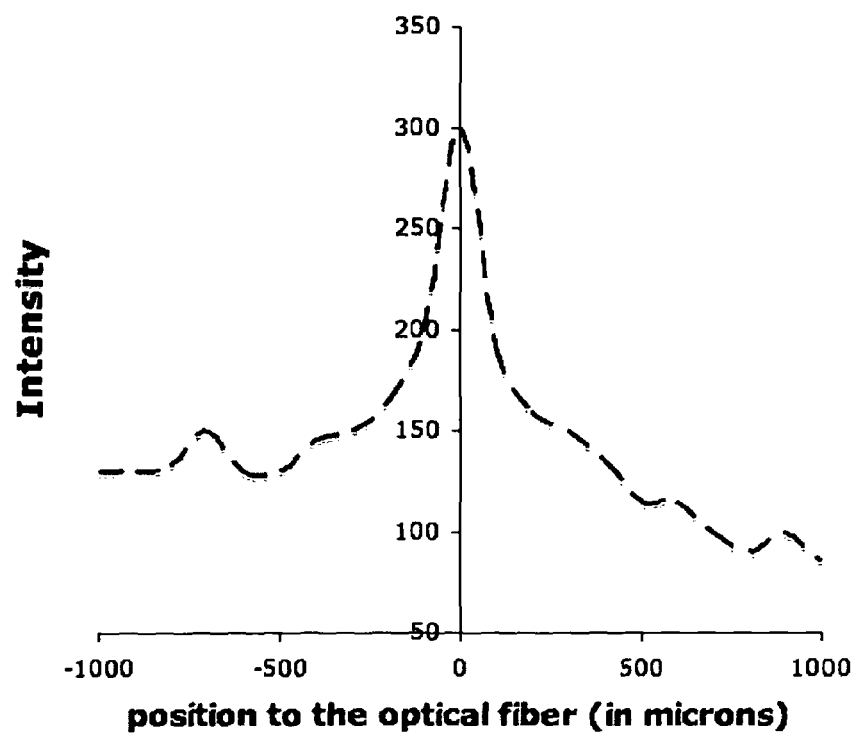
Figure 21B:
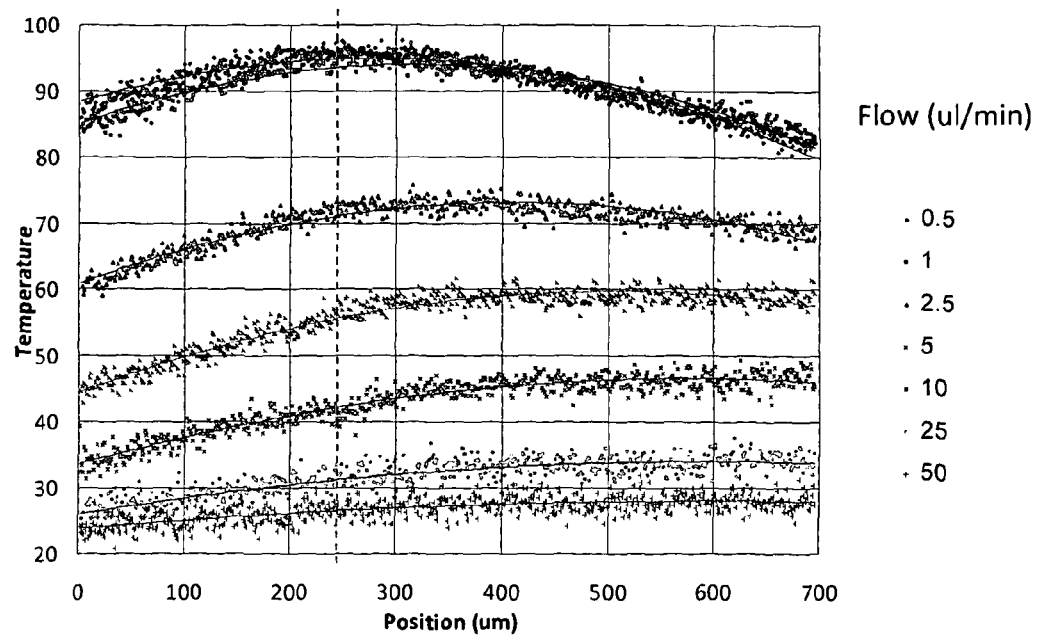
Figure 22:
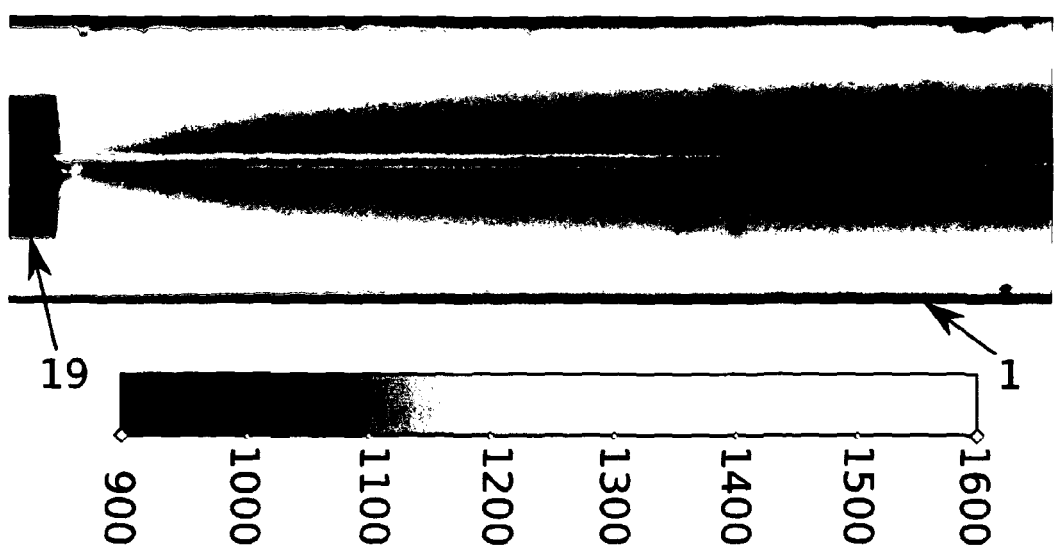
Figure 23:
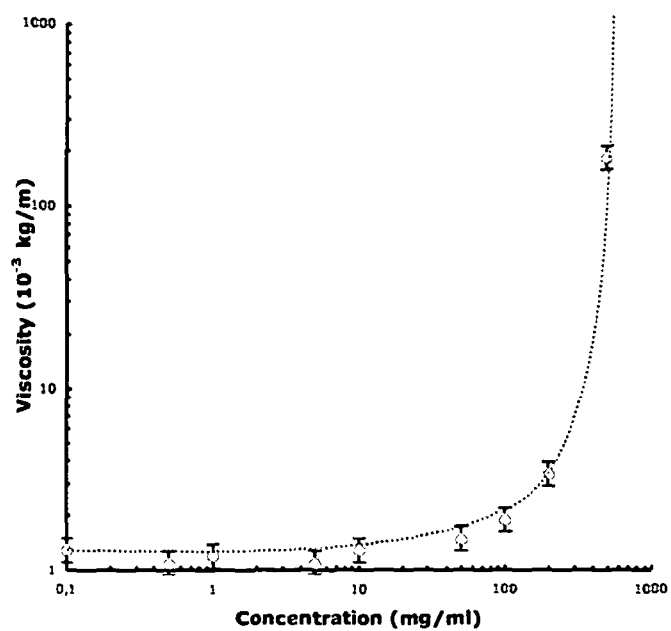

FIG. 21A shows the intensity variation of TAMRA fluorescence as a function of distance along a channel from the site of IR excitation (24 mW, 1550 nm). IR radiation was carried through an optical fibre perpendicular to the wall of the capillary containing the stationary TAMRA sample. Fluorescence intensity of the TAMRA was measured using confocal microscope with excitation wavelength of 543 nm and emission wavelength of 608 nm;

FIG. 21B shows the intensity variation of TAMRA fluorescence as a function of position in a channel relative to the site of excitation (60 mW, 0.025 mg/ml TAMRA, 50 mM Tris buffer at pH 7.2). IR radiation was carried through an optical fibre perpendicular to the wall of the capillary containing the stationary TAMRA sample, the position of the centre of the optical fibre was 246 μm. This figure shows the temperature gradient that can be obtained using the device of FIG. 2B;

FIG. 22 shows the intensity variation of TAMRA fluorescence as a function of position in a channel relative to the site (19) of IR excitation (24 mW, 1550 nm). IR radiation was carried through an optical fibre within the capillary containing the TAMRA sample flowing in the same direction as the radiation at 100 μL min$^{-1}$. Fluorescence intensity of the TAMRA was measured using confocal microscope with excitation wavelength of 543 nm and emission wavelength of 608 nm; and FIG. 23 shows the variation of the viscosity of a BSA solution as a function of its concentration.

DETAILED DESCRIPTION

Figure 1A:
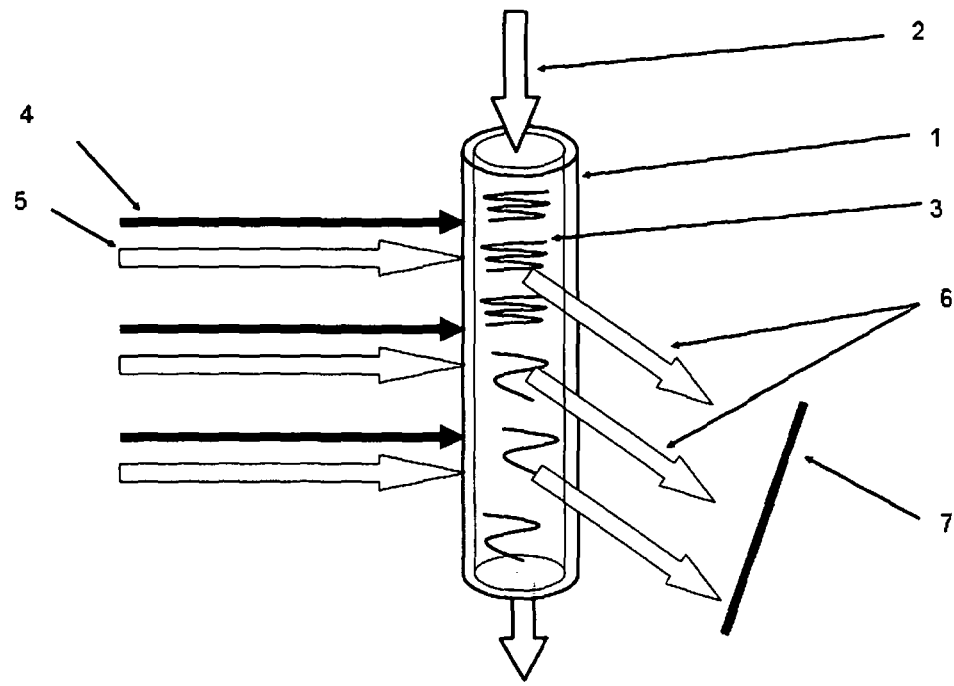
FIG. 1A is a schematic representation of a channel for use in the device of the invention illustrating the focusing of both IR and UV radiation perpendicular to sample flow, with detection of the resulting fluorescence.
Figure 1B:
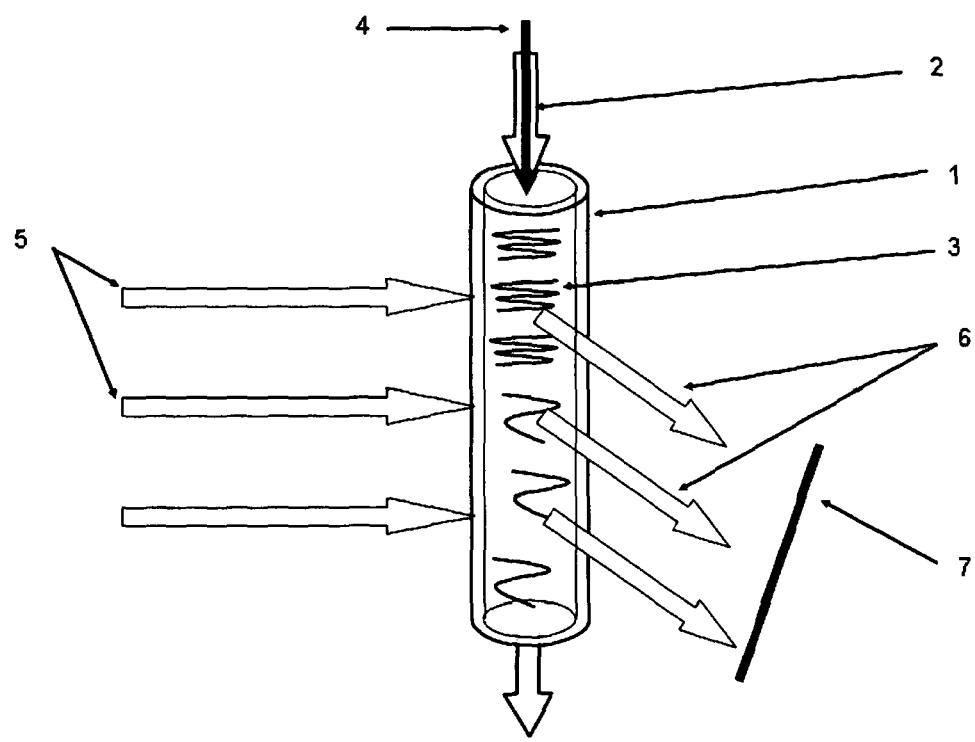
FIG. 1B is a schematic representation of a channel for use in the device of the invention illustrating the focusing of IR radiation parallel to sample flow, the application of UV radiation perpendicular to the sample flow, with detection of the resulting fluorescence.

The device of the invention may include the elements illustrated schematically in FIGS. 1A and 1B. A capillary 1 contains a flowing sample 2 in which is dissolved a biological molecule such as a protein 3. An infrared laser or LED 4, of wavelength preferably in the range 1400-1600 nm, is focused onto the sample in the capillary 1. A second laser or LED 5, preferably producing deep UV (250-300 nm) or blue light, is also focused on the sample in the capillary to fluorescently excite the sample, this results in a longer wavelength fluorescent emission 6 recorded using a detector 7 such as a CCD camera, photodiode, or photo-multiplier tube (PMT). At least two alternative configurations are possible. For example, in FIG. 1A heating of the sample is achieved by infra-red radiation focused onto a capillary perpendicular to the sample flow at one or more points along the channel length. Fluorescence detection is perpendicular to the sample flow. This configuration allows one or more points of both heating and fluorescence detection. In FIG. 1B, heating of the sample is achieved by infra-red radiation focused onto a capillary in parallel to the sample flow. Fluorescence detection is perpendicular to the sample flow. This configuration allows a single IR radiation source to continually heat the sample along the length of the capillary, while also allowing one or more points of fluorescence detection.

Figure 2A:
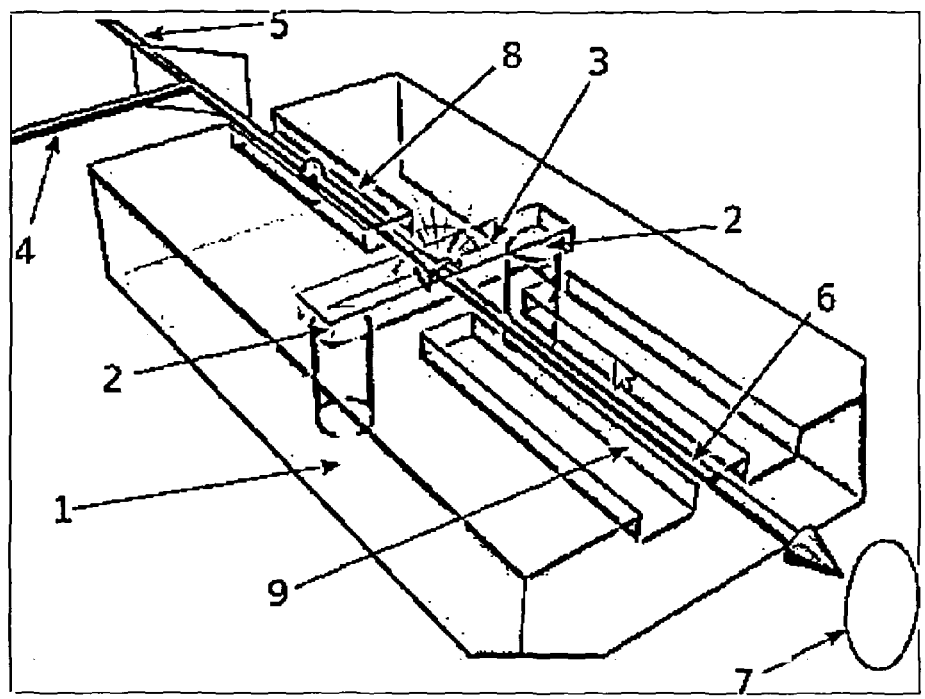
FIG. 2A is a schematic representation of the device of the invention illustrating a channel cavity and waveguides in a chip with one measurement point.
Figure 2B:
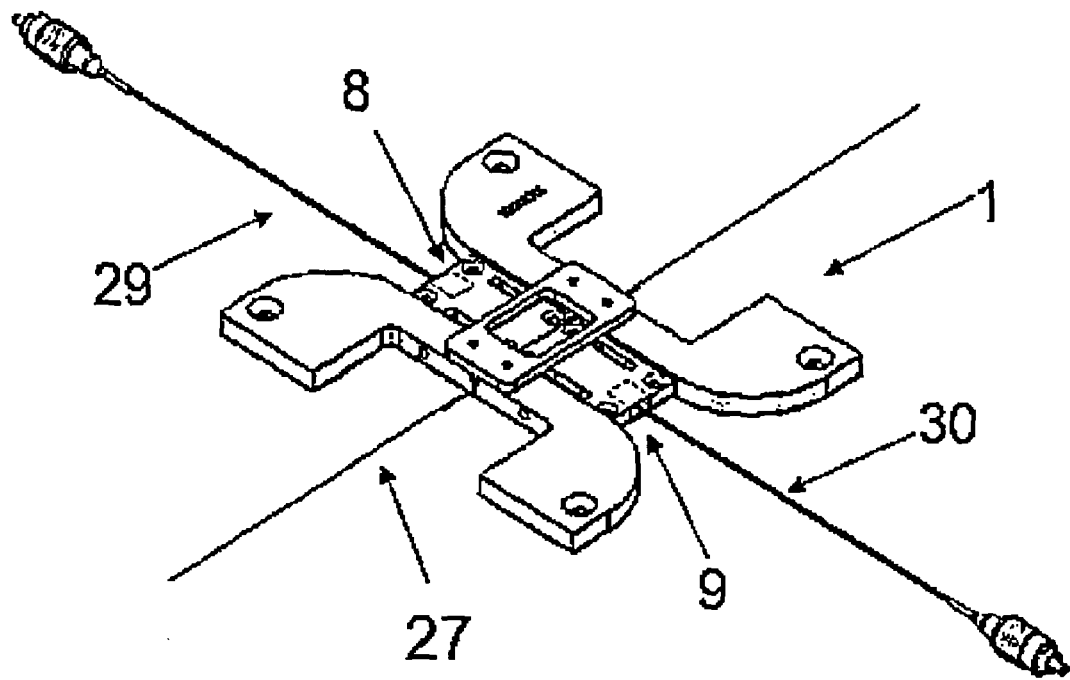
FIG. 2B is a device of the invention illustrating a channel cavity and waveguides.

As shown in FIG. 2A, the design can be further integrated into a chip 1 by the use of an optical waveguide 8 that allows the simultaneous transmission of infra-red 4 and UV excitation 5 radiation sources up to the edge of a microfluidic channel 3. A second waveguide 9 emanating from the same point along the channel can then be used to transmit the fluorescence emission signal 6 to a detector 7. The key features shown are the integration of localised heating of a small sample volume using the infrared laser with fluorescence measurements at the same location. A variation of this configuration could place separate waveguides adjacent to each other, with one for the infra-red source and the second (downstream in the sample flow) for the UV radiation source. Multiple points of heating and fluorescence detection can be achieved by using waveguides, optical fibres or lenses arrayed along a small length of the channel to obtain a temperature gradient along the channel. This configuration would, for example, make it possible to collect a complete protein thermal denaturation curve from simultaneous measurements along the length of the channel. FIG. 2B shows another form of the device of the invention in which the channel cavity is a capillary tube 27 and the waveguides 8, 9 carry optical fibers 29, 30. The device of FIG. 2B is a flow device, wherein the capillary tube 27 carries the sample to a position intersecting the optical fibers 29, 30 where excitation and signal emission, or where IR heating occur. This device is also compatible with a confocal microscope stage to allow additional measurement from above the capillary tube 27 of signal emissions from the capillary tube 27.

Figure 3A:
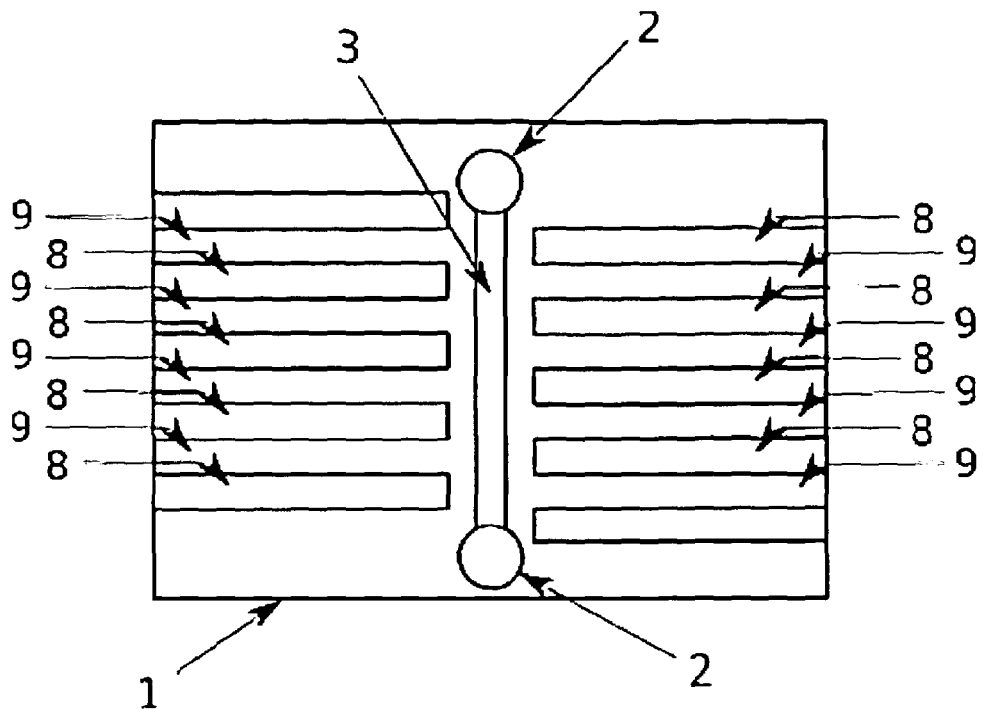
FIG. 3A is a schematic representation from above of a possible configuration of waveguides relative to a channel cavity.

FIG. 3 illustrates several chips which implement the basic invention. The first (FIG. 3A) contains a single channel 3 addressed via multiple optical waveguides 8, 9, on a monolithic chip 1. This configuration could easily be scaled out to multiple sample channels (not shown) on a single chip.

Figure 3B:
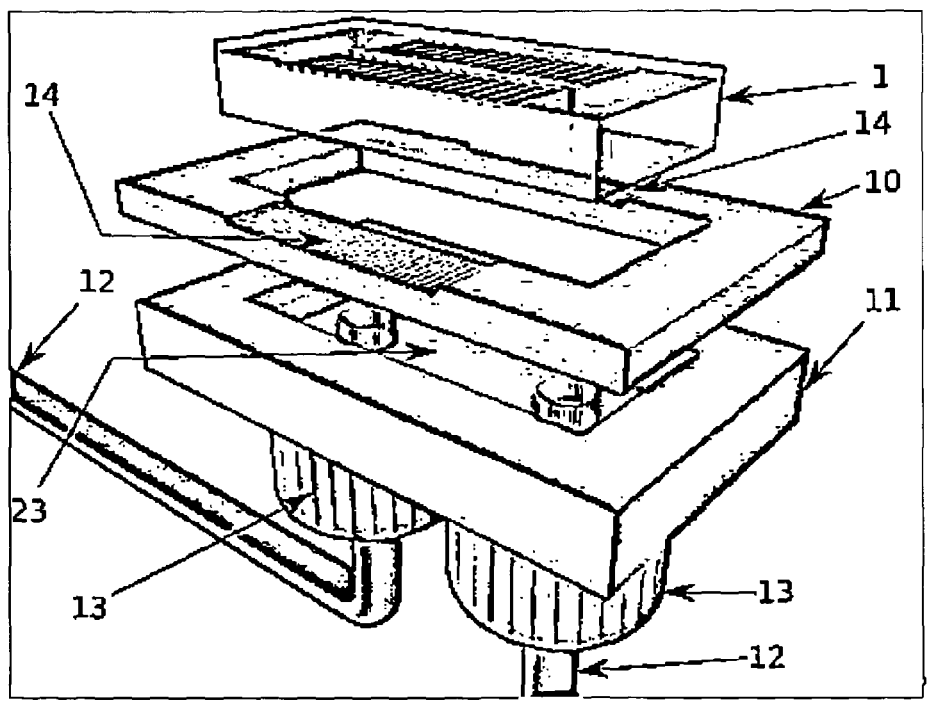
FIG. 3B is an exploded view of a device of the invention including a motherboard.
Figure 3C:
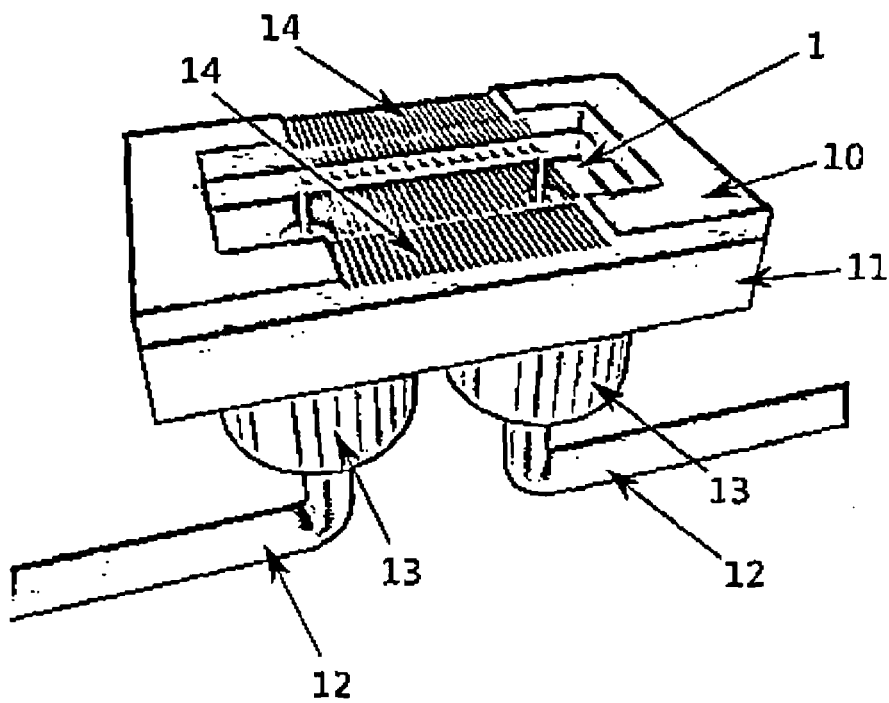
FIG. 3C is a view of the device of FIG. 3B when assembled.

FIGS. 3B and 3C show a microfluidic device in which a disposable chip 1 (as in FIG. 3A), is decoupled from a fixed "motherboard" 10, 11 on which the lasers and fluid pump tubes 12 are affixed. Included is a mechanical system for assuring accurate alignment of the disposable chip's optical waveguides 8, 9 and sample flow entry and exit points 2 to the motherboard, while retaining a simple mechanism to exchange the disposable chip. The chip waveguides 8, 9 should align to the waveguides 14 of the optical component of the motherboard 10 to which the lasers and detector are mounted and aligned. The optical component of the motherboard 10 may itself be fabricated separately to the fluidic motherboard 11 using a different material. Meanwhile the channel entry and exit points 2 align and form a tight connection to the fluid connectors 13 on the motherboard base 11. The disposable chip is preferably made out of plastic (e.g. SU8 or PDMS) or silicon.

Figure 4:
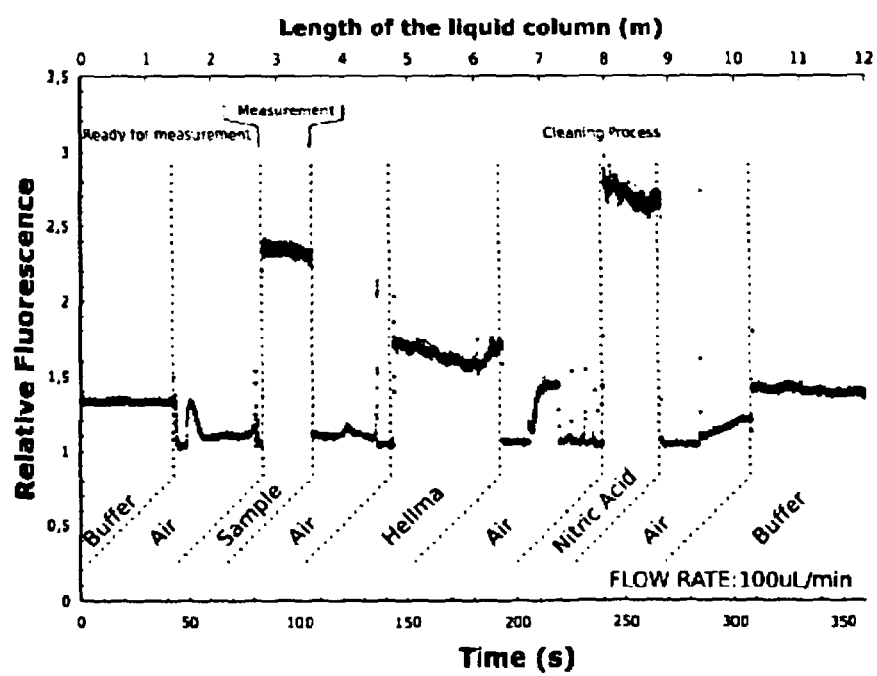
FIG. 4 shows the output for one complete cleaning cycle, including sample fluorescence measurement and channel cleaning.

Cleaning of the chip can be effected by sequential flushing of the cavity with 1% Hellmanex® II, 2% nitric acid, air, and sample buffer. Flush duration for this example is 5 minutes for each cleaning solution and the buffer, with flush rates of around 10 µl min$^{-1}$ for the cleaning solutions and around 40 µl min$^{-1}$ for the buffer. In flow systems, cleaning may be achieved as part of a continuous process with bubbles of sample being passed through the cavity, followed by air, cleaning solution, air, buffer, and further samples. The air separates and prevents mixing of the respective liquids. FIG. 4 illustrates the cleaning process described above.

The first and second radiation sources are monochromatic and this can be achieved using filters, gratings or other devices, and focused if necessary using lenses, prior to transmission into the waveguides, all available to those skilled in the art. The excitation signal from fluorescence can be detected using lenses, filters, or gratings in series to modify or focus the signal before detection by a photomultiplier tube (PMT), CCD camera, photodiode or other detection method available to those skilled in the art.

All of these peripheral elements for radiation input and detection can alternatively be integrated onto a single device endowed with optical and microfluidic functionalities using combinations of planar optical waveguides, optical fibres, lasers, gratings, filters and detectors.

Operation of the device is not limited to duplication of the standard continuous wave (CW) procedure used in current plate readers. In particular, it is possible to take advantage of pulsing both the IR and fluorescence-inducing lasers, as well as measuring time-dependent fluorescent emissions and optical attenuation and scattering signals using the detectors. Such measurements can be used to analyse changes in parameters such as the molecular size, or the rotation and diffusion of proteins as a function of thermal perturbations.

The temperature gradient within the sample along the length of the channel can be calibrated by using thermally sensitive fluorescent or luminescent agents flowed through the device microfluidic channel. The fluorescence or luminescence at multiple points along the channel can be determined using the integrated fluorescence detection optics, or using a confocal microscope. This eliminates the need for a thermocouple or other temperature sensing device to be manufactured as part of the chip or motherboard. It also takes advantage of the same optics used in the device to measure the conformation (or concentration) of sample molecules.

EXAMPLES

Source of Samples

Rapamycin was from LC Laboratories (Woburn, Mass., USA). All other reagents were from Sigma-Aldrich. Wild-type FKBP-12 and the F99L mutant were expressed and purified from a GST-FKBP fusion gene of the pGST-FKBP-12 plasmid in *E. coli* BL21 cells as described in Main, E. R., Fulton, K. F., & Jackson, S. E. Folding pathway of FKBP12 and characterisation of the transition state. *J. Mol. Biol.* 291, 429-444 (1999).

Experimental Demonstration and Development of the Micro Fluidic System

Example 1

Protein Intrinsic Fluorescence Detection in a Capillary

Figure 5:
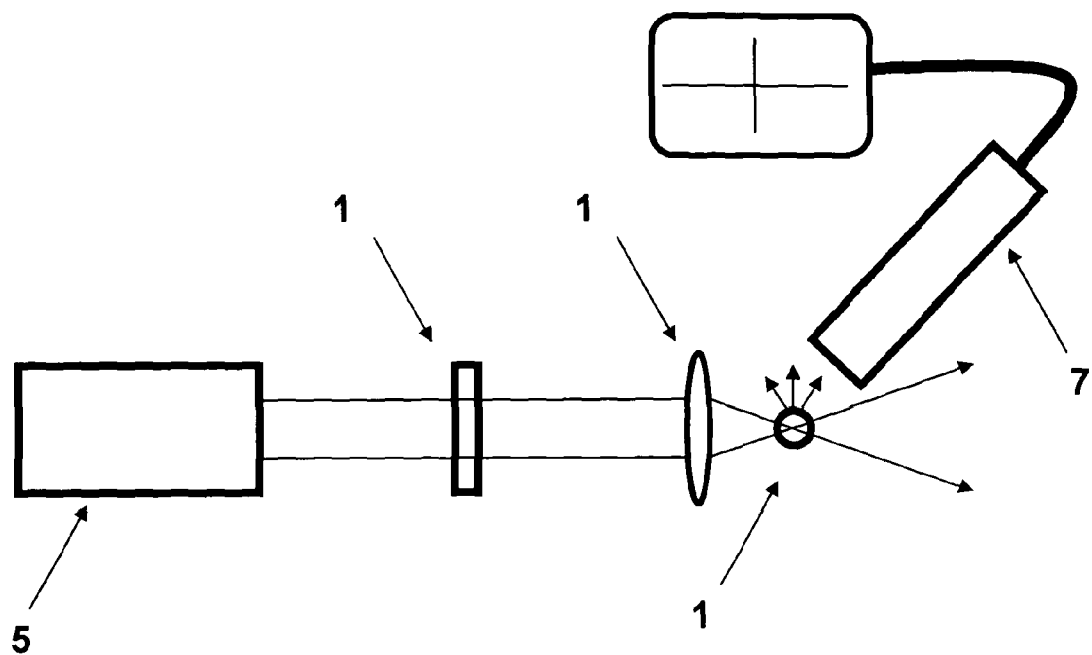
FIG. 5 is a schematic representation of the use of the device in the measurement of protein UV fluorescence.

FIG. 5 shows a possible configuration for the use of the device. The configuration comprises a laser 5 (QUV266-02, Crystalaser, Reno, Nev.) of wavelength 266 nm, 5 mW, pulsed at 1 kHz; a bandpass filter (newport), at 266 nm 15; a converging lens (SPX010AR.10, Newport) 16; a 100 µm internal diameter capillary (FS-110, Upchurch™) 1; and a photo multiplier tube (R1166PMT, Hamamatsu, Japan) 7; linked to a data acquisition system consisting of a PC expansion card (PXI-5124, National Instruments), for capture and analysis of the data in Labview (National Instruments). The configuration of FIG. 5 has been used to measure the effect of the concentration of bovine serum albumin (BSA) in solution upon the intensity of intrinsic fluorescence obtained at a flow rate of 10 µl/min by a syringe pump (KD Scientific Inc., Holliston, Mass.) and a 500 µl Hamilton gas-tight syringe. Samples were measured and averaged for 100 laser pulses.

Figure 6:
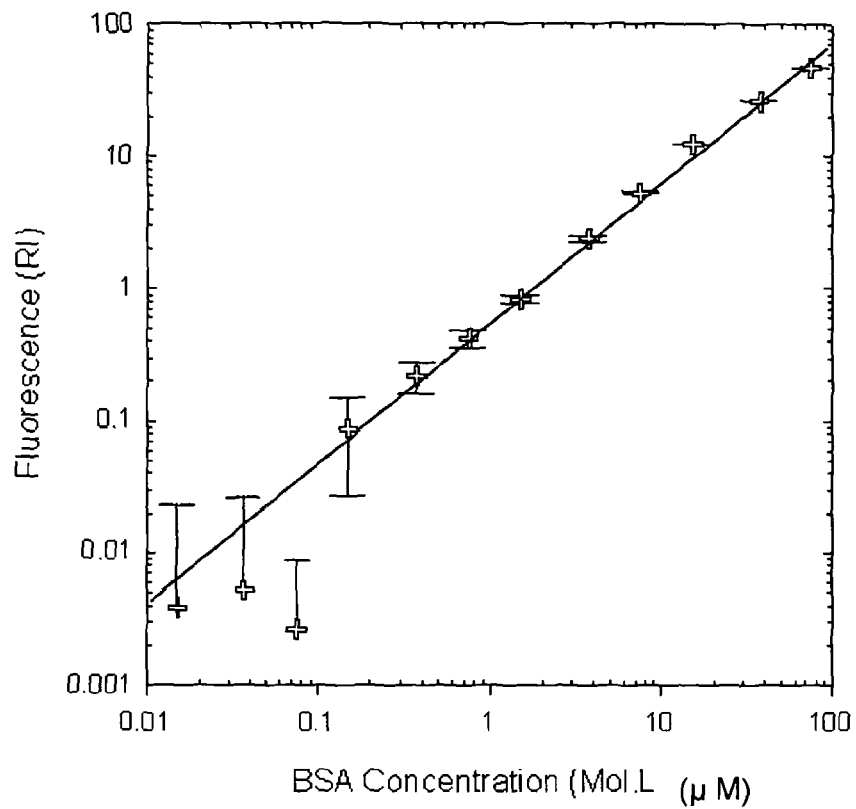
FIG. 6 shows the intrinsic fluorescence of bovine serum albumin (BSA) as a function of concentration in a capillary of 100 μm internal diameter.

The excitation at 266 nm generated reemission at 340 nm, as shown in FIG. 6. This graph demonstrates the linearity between the fluorescence intensity measured and the protein concentration. A fluorescence relative intensity of 1500 at a concentration of 0 mg ml$^{-1}$ of BSA corresponds to the background signal of the setup generated by excitation radiation. The use of a monochromated or filtered 266 nm source attenuates this background signal.

Figure 7:
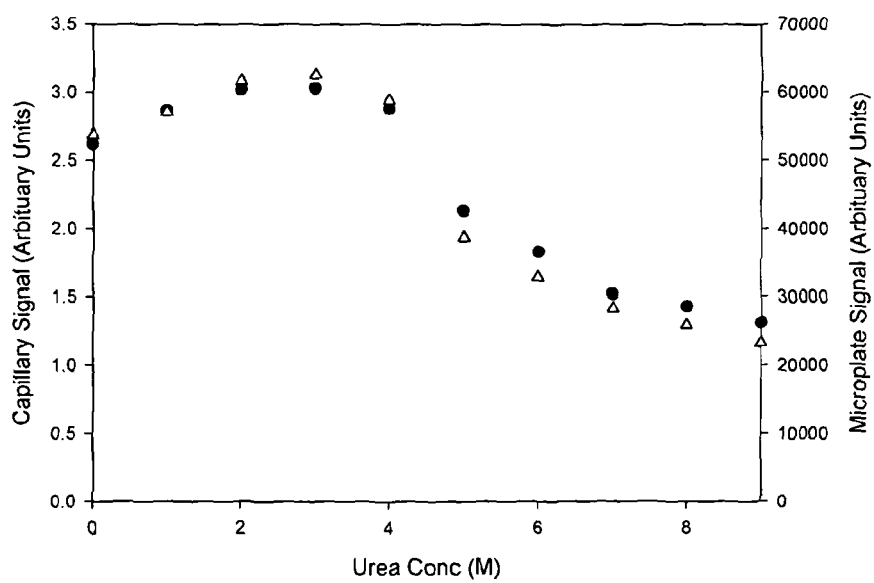
FIG. 7 shows the intrinsic fluorescence intensity of 5 mg/ml BSA as a function of urea concentration, in Tris.HCl pH 7, obtained by the capillary method (filled circles), and for comparison using a BMG Labtech microplate reader in 96-well microplates (open triangles)

Another experiment was performed to determine the dependence of the intrinsic fluorescence of 0.5 mg ml$^{-1}$ BSA on the concentration of the chemical denaturant urea over the range that is known to unfold the protein, using a flow rate of 10 μl/min. The results of this experiment are presented in FIG. 7 alongside data obtained using a BMG-labtech Fluostar (Aylesbury, UK) plate reader and a 96-well plate. The two curves are in close agreement, thus demonstrating the accuracy of the capillary-based intrinsic fluorescence measurement. The increasing urea concentration progressively denatures the BSA protein resulting in a decrease in the intrinsic fluorescence intensity of the protein. The denaturation profile is sigmoidal as is typical for proteins and represents a two-state transition as observed by this method due to a population change from predominantly the native-state to predominantly the denatured protein whereby each state gives a different intrinsic fluorescence intensity. The mid-point of the transition occurs at a concentration of 4.5M urea.

Figure 8:
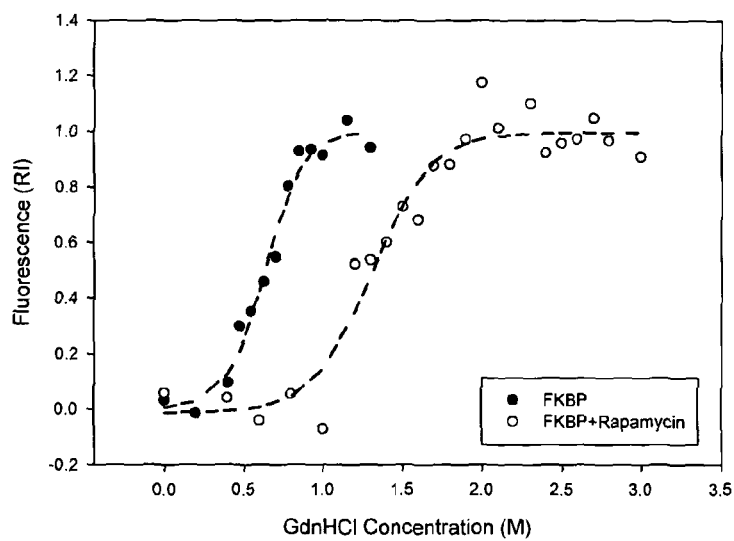
FIG. 8 shows the intrinsic fluorescence intensity of 2 μM FKBP-12 as a function of urea concentration, in Tris.HCl pH 7, in the presence (open circles) and absence (closed circles) of 20 μM rapamycin.

The denaturation experiment was repeated for another protein using 2 μM FKBP-12. The goal of this experiment was to demonstrate the possibility of measuring the binding of a ligand molecule (rapamycin) to a protein (FKBP 12) due to the increase in stability upon ligand binding. The stability was measured using the denaturant guanidinium hydrochloride (GdHCl) in 1 mM dithiothreitol (DTT), 50 mM Tris.HCl at pH 7.5 and at 20° C., using a flow rate of 10 μL/min through the capillary. The fluorescence of FKBP with various concentrations of GdHCl (from 0M to 3M) was measured. In a second experiment FKBP12 was used at the same concentration (2 μM) but now pre-incubated with rapamycin (20 μM) for various concentration of GdHCl (from 0M to 3M). The fluorescence values for the two experiments are shown in FIG. 8. An increase in the mid-point of denaturation ($C_{1/2}$) is observed upon incubation with the rapamycin. $C_{1/2}$ represents the denaturant concentration at which half of the protein is in the unfolded state. In the absence of rapamycin it is 0.65M GdHCl for FKBP12, whereas in the presence of 20 μM rapamycin it is 1.35M GdHCl. This demonstrates that the rapamycin can bind to FKBP-12. The dissociation constant for this interaction can be determined from the difference in their denaturation mid-points.

Example 2

Figure 9:
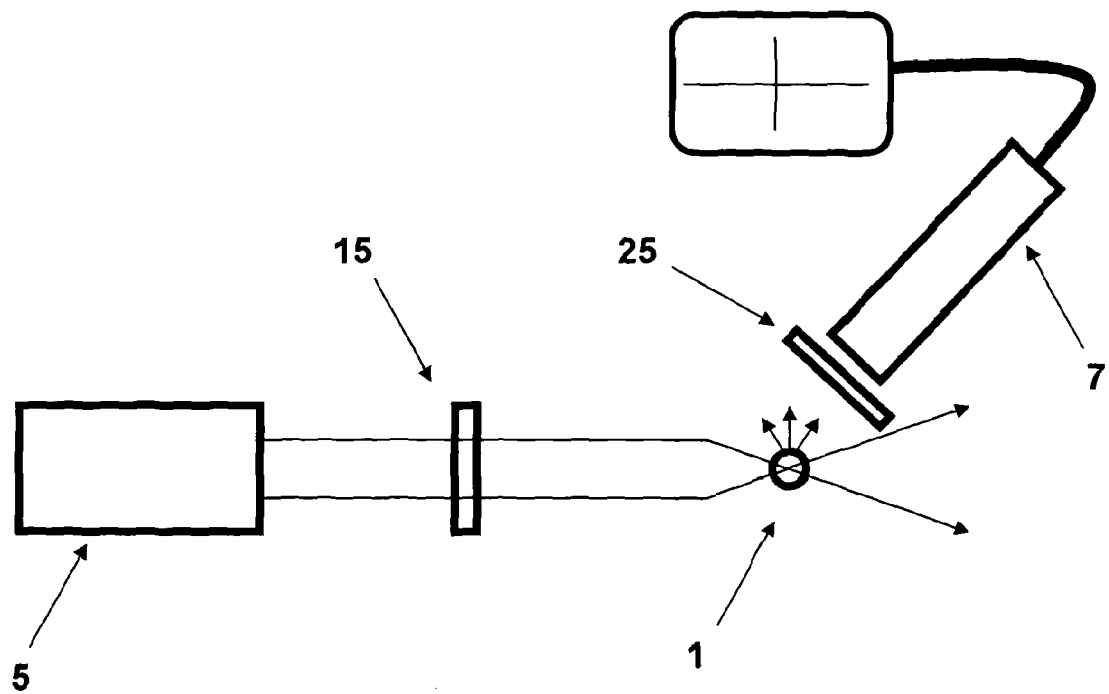
FIG. 9 is a schematic representation of the use of the device in the measurement of protein UV fluorescence.
Figure 10:
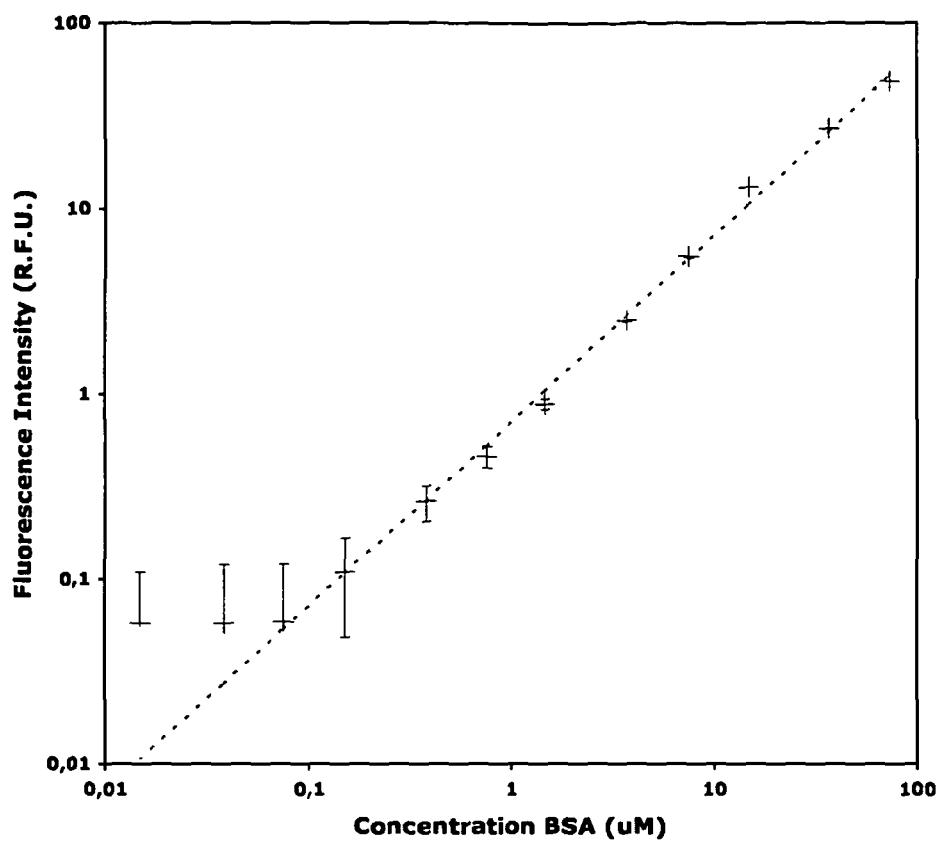
FIG. 10 shows the linearity and sensitivity of fluorescence intensity measurements in the inventive device.

Comparison of Protein Intrinsic Fluorescence Detection in a Capillary and in a Microplate To illustrate the flexibility of the devices of the invention, an alternative configuration was used to show the uses of the invention in the intrinsic fluorescence detection of proteins. FIG. 9 shows this alternative configuration for the use of the device. As with the configuration of Example 1, the configuration comprises a laser 5 (QUV266-02, Crystalaser, Reno, Nev.) of wavelength 266 nm, 5 mW, pulsed at 1 kHz; a bandpass filter (newport), at 266 nm 15; a 100 μm internal diameter capillary (FS-110, Upchurch™) 1; and a photo multiplier tube (R1166PMT, Hamamatsu, Japan) 7; linked to a data acquisition system consisting of a PC expansion card (PXI-5124, National Instruments), for capture and analysis of the data in Labview (National Instruments). In this embodiment, converging lens 16 is absent, but a dichroic mirror (Andover, Salem, N.H.) 25 is present to filter the fluorescence emission so that only emission in the range 320-400 nm passes to the photo multiplier 7. The configuration of FIG. 9 has been used to measure the effect of the concentration of BSA in solution upon the intensity of intrinsic fluorescence obtained at a flow rate of 10 μl/min by a syringe pump (KD Scientific Inc., Holliston, Mass.) and a 500 μl Hamilton gastight syringe. Twelve solutions of BSA at 0.015 μM to 75 μM were prepared in 60 mM sodium phosphate buffer, pH 7.0. Samples were measured and averaged for 100 laser pulses. The fluorescence intensities of BSA solutions at different protein concentrations are shown in FIG. 10. Fluorescence intensities are shown in relative fluorescence units (RFU) measured at a range of bovine serum albumin (BSA) concentrations in sodium phosphate buffer, pH 7.0, 21° C. using the capillary technique. Each data point was obtained from an average of 100 laser pulses at 1 kHz. Error bars shown are standard deviations. The dashed curve shows a linear fit to the logarithmic data.

The fluorescence emission observed using the device of the invention was linearly proportional to the protein concentration with an $R^2$ of 0.994, and a standard error for each measurement of 0.015 RFU at above 1.5 μM BSA (from 100 laser pulses). The dynamic range of the linear response was 0.15 μM (0.01 mg/ml) to at least 75 μM (5 mg/ml) of BSA, corresponding to 0.45 to 225 μM tryptophan residues. The limit of detection was 0.15 μM BSA, and the signal-to-noise based on the standard deviation value ranged from 1.27 at 0.15 μM to 1568 at 75 μM BSA. The background fluorescence of the buffer was subtracted from all measurements and had a relative fluorescence intensity of 16.15 with a signal-to-noise of 323. To maintain the dynamic range and sensitivity the voltage applied to the PMT was altered from 500 V for measurements between 1.5 μM and 75 μM BSA, to 600 V for less than 1.5 μM. The higher PMT voltage resulted in an increased (electronic) noise-induced measurement error.

The detection limits obtained in the technique of the invention were compared to that obtained in a microplate (see Table 1). While the microplate reader was able to detect approximately half the concentration of BSA, the volume required was over $10^5$ times greater than for the capillary technique of the invention. This gave a limit of detection of $1.4 \times 10^8$ protein molecules in the capillary, which is 85,000-fold lower than for the microplate reader.

TABLE 1

Limits of detection for BSA using fluorescence at different scales

| Technique | Minimum [Protein] (μM) | Measurement Volume (L) | Number of protein molecules |
|---|---|---|---|
| Microplate | 0.076 | $2.6 \times 10^{-4}$ | $1.16 \times 10^{13}$ |
| Micro-capillary | 0.15 | $1.5 \times 10^{-9}$ | $1.4 \times 10^8$ |

The effect of urea denaturant concentration upon the measured fluorescence intensity of a 7.14 μM BSA solution at pH 7.2 is shown in FIG. 11 for both the capillary-based and microplate methods. The experimental method required that 2 mL each of a range of urea solutions from 0 M to 9 M in 50 mM Tris.HCl, pH 7.2 be added 100 μL 0.15 mM BSA stock (250 mg BSA in 25 mL 50 mM Tris.HCl, pH 7.2), giving final BSA concentrations of 7.14 μM. Samples were equilibrated for 17 hours at 22° C., consistent with the FKBP-12 experiments below. Fluorescence intensities were measured in the capillary as above, and then in a Fluostar Optima plate-reader (BMG Labtechnologies, Aylesbury, UK) with 280 nm excitation and 340±10 nm emission as described in Aucamp, J. P., Cosme, A. M., Lye, G. J., & Dalby, P. A. High-throughput measurement of protein stability in microtiter plates. *Biotechnol Bioeng* 89, 599-607 (2005) and Aucamp, J. P., Martinez-Tones, R. J., Hibbert, E. G., & Dalby, P. A. A microplate-based evaluation of complex denaturation pathways: structural stability of *Escherichia coli* transketolase. *Biotechnol. Bioeng.* 99, 1303-1310 (2008).

Figure 11A:
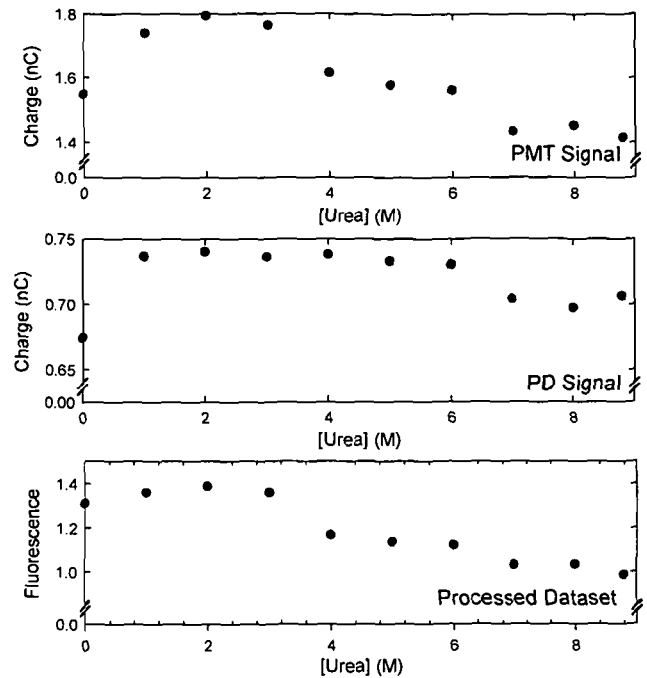
FIG. 11 shows fluorescence intensity measurements of BSA denaturation at equilibrium.
Figure 11B:
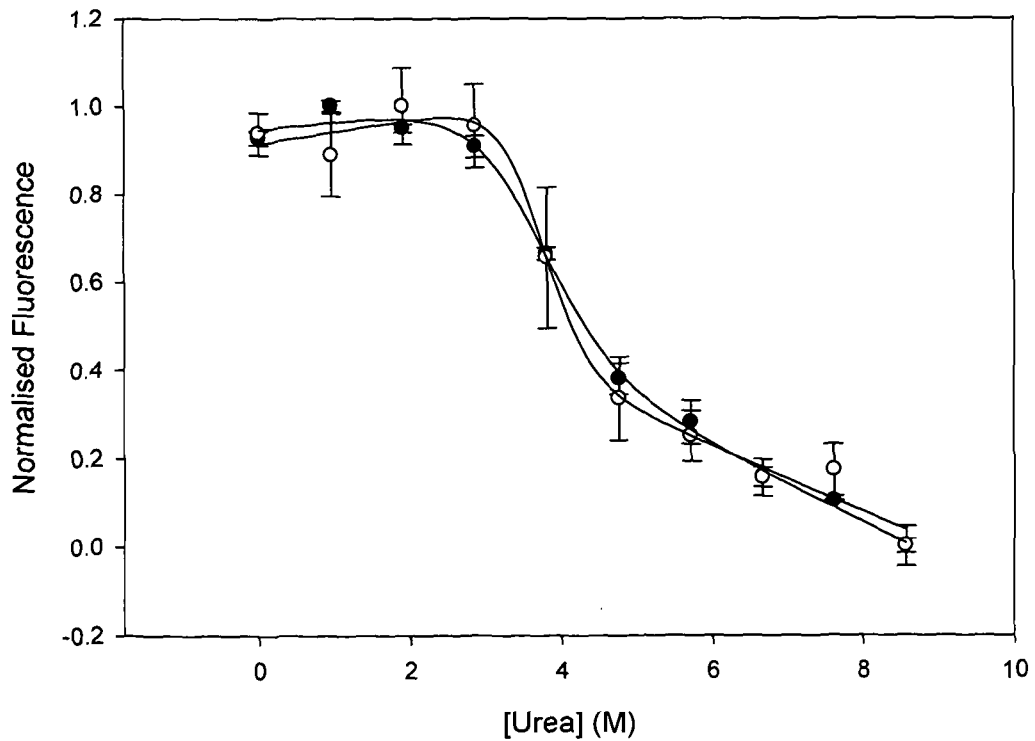

FIG. 11A is raw data obtained in the inventive method for a single replicate as fluorescence emission at the photomultiplier tube (PMT) and excitation laser intensity at the photodiode (PD) for a typical denaturation curve acquisition. The final fluorescence measurement (labelled "processed dataset") was obtained as the ratio of the PMT to the PD signals, to account for time-dependent variations of the incident laser source between measurements, with a similar ratio for the blank subtracted. These data are then normalised to unity for high [urea] to produce the curves shown in panel b. FIG. 11B is a comparison of the inventive device (open symbols) and 96-well microplate-based (closed symbols) equilibrium denaturation of 7.14 μM BSA by urea as measured by the change in the normalised intrinsic fluorescence intensity of samples in 50 mM Tris.HCl, pH 7.2, 22° C. Error bars shown are standard deviations from triplicate measurements. The best fits to the equation below are also shown for each dataset.

$$F_{obs} = \frac{(F_N^0 + m_N[D]) + e^{\left(\frac{m_G[D-C_{1/2}]}{RT}\right)}(F_U^0 + m_U[D])}{e^{\left(\frac{m_G[D-C_{1/2}]}{RT}\right)} + 1}$$

The raw data in FIG. 11A demonstrates the need for continuously monitoring the incident laser intensity with a photodiode and also illustrates the good signal-to-noise ratio obtained with BSA. A sharp sigmoidal transition is observed, as expected for the cooperative two-state unfolding of proteins upon addition of a chemical denaturant. The thermodynamic parameters obtained by fitting the data to the equations below are shown in Table 2.

$$F_{obs} = \frac{(F_N^0 + m_N[D]) + e^{\left(\frac{m_G[D-C_{1/2}]}{RT}\right)}(F_U^0 + m_U[D])}{e^{\left(\frac{m_G[D-C_{1/2}]}{RT}\right)} + 1}$$

$$\Delta G_{obs} = \Delta G_{H_2O} + m_G[D]$$

TABLE 2

Thermodynamic parameters for the denaturation of BSA, FKBP-12 wt and FKBP-12 F99L

| Experiment | $C_{1/2}{}^a$ (M) | $m_G$ (kcal mol$^{-1}$ M$^{-1}$) | $\Delta G_{<mG>}{}^b$ (kcal mol$^{-1}$) | $\Delta G_{H2O}{}^c$ (kcal mol$^{-1}$) | $\Delta\Delta G_{X-WT}{}^d$ (kcal mol$^{-1}$) |
|---|---|---|---|---|---|
| | | Capillary method | | | |
| FKBP-12 wt | 0.74 ± 0.02 | 5.4 ± 0.7 | 3.84 ± 0.3 | 4.03 ± 0.5 | 0 |
| FKBP-12 wt + Rapamycin | 2.28 ± 0.02 | 3.5 ± 0.3 | 7.70 ± 0.5 | 8.08 ± 0.7 | 4.05 ± 0.9 |
| FKBP-12 F99L | 0.63 ± 0.03 | 4.9 ± 0.8 | 3.26 ± 0.3 | 3.11 ± 0.5 | −0.92 ± 0.7 |
| FKBP-12 F99L + Rapamycin | 1.31 ± 0.05 | 3.2 ± 0.7 | 4.41 ± 0.3 | 4.20 ± 0.9 | 0.17 ± 1.0 |
| BSA | 3.7 ± 0.2 | 1.9 ± 0.2 | na | 7.0 ± 0.8 | na |
| | | Microplate method | | | |
| FKBP-12 wt | 0.77 ± 0.01 | 6.6 ± 0.4 | 4.72 ± 0.3 | 5.05 ± 0.3 | 0 |
| FKBP-12 wt + Rapamycin | 2.36 ± 0.01 | 3.7 ± 0.2 | 8.26 ± 0.4 | 8.73 ± 0.4 | 3.68 ± 0.5 |
| FKBP-12 F99L | 0.69 ± 0.01 | 5.7 ± 0.4 | 4.23 ± 0.3 | 3.9 ± 0.3 | −1.15 ± 0.4 |
| FKBP-12 F99L + Rapamycin | 1.53 ± 0.01 | 3.3 ± 0.2 | 5.36 ± 0.3 | 5.05 ± 0.3 | 0 ± 0.4 |
| BSA$^e$ | 3.6 ± 0.2 | 1.2 ± 0.2 | na | 4.4 ± 0.8 | na |
| | | Literature | | | |
| FKBP-12 wt$^f$ | 0.78 ± 0.005 | 6.6 ± 0.3 | na | 5.13 ± 0.2 | 0 |
| FKBP-12 wt + Rapamycin$^f$ | 2.10 ± 0.01 | 3.9 ± 0.3 | na | 8.21 ± 0.6 | 3.08 ± 0.6 |

All errors quoted on $C_{1/2}$ and $m_G$ are curve fit errors given in Sigmaplot (Systat Software, Hounslow, UK) which indicate the range of values possible without significantly altering $R^2$ for the fit. Wild-type FKBP-12 measurements were at 10 μM protein, and FL99 FKBP-12 at 11.1 μM, 50 mM Tris.HCl, pH 7.5, 1 mM DTT
$^a$Transition mid-points are quoted for GdnHCl as denaturant except for BSA where urea was used
$^b\Delta G_{<mG>}$ values were obtained using the average $m_G$ values for each protein type
$^c\Delta G_{H2O}$ values were obtained using the $m_G$ values from each independent curve fit
$^d\Delta\Delta G_{X-WT}$ values are all relative to wild-type FKBP-12 without rapamycin and are obtained from $\Delta G_{H2O}$ values.
$^e$From Aucamp, J. P., Cosme, A. M., Lye, G. J., & Dalby, P. A. High-throughput measurement of protein stability in microtiter plates. *Biotechnol Bioeng* 89, 599-607 (2005)
$^f$From Main, E. R. & Jackson, S. E. Does trifluoroethanol affect folding pathways and can it be used as a probe of structure in transition states? *Nat. Struct. Biol.* 6, 831-835 (1999)

As can be seen, transition midpoints ($C_{1/2}$), of 3.7±0.2 M and 3.6±0.2 M were obtained by the capillary and microplate techniques respectively.

The results above clearly demonstrate that the use of a capillary-based fluorescence technique falling within the scope of the invention can be used to derive a range of thermodynamic parameters.

Chemical denaturation of wild-type and the mutant FL99 of FKBP-12 by guanidine hydrochloride (GdnHCl) was carried out in a microplate using the technique described in Aucamp, J. P., Cosme, A. M., Lye, G. J., & Dalby, P. A. High-throughput measurement of protein stability in microtiter plates. *Biotechnol Bioeng* 89, 599-607 (2005) and the same samples were then measured directly afterwards using the inventive technique. The experimental detail was as set out below:

Equilibrium denaturation of wild-type FKBP-12: 50 µl, of FKBP-12 stock (50 µM FKBP-12, 5 mM DTT, 50 mM Tris.HCl, pH 7.5) was added to each well of a UV transparent Costar (Corning, Lowell, Mass., USA) 96-well plate. Twenty-five concentrations of guanidine hydrochloride (GdnHCl) from 0 to 5.6 M, were created by varying the volumes of 0 M and 7 M GdnHCl stock solutions in 50 mM Tris.HCl pH 7.5, autotitrated in each well (Fluostar Optima) to a total of 200 µL. For rapamycin binding, the 0 M and 7 M GdnHCl stock solutions both contained 18.8 µM rapamycin (from a 54 mM stock in EtOH), giving a 15 µM final concentration. Samples were sealed and equilibrated for 17 hours at 22° C. prior to measurement of intrinsic protein fluorescence in a Fluostar Optima plate reader as above. The same samples were then used to measure intrinsic protein fluorescence in the micro-capillary device for a direct comparison.

Equilibrium denaturation of mutant FKBP-12 (F99L): Samples were prepared and analysed as above for wild type, except that 25 µL of 100 µM FKBP-12 F99L in 50 mM Tris pH 7.5, 1 mM DTT was added to each well. Also, each concentration of GdnHCl was obtained using 0 and 4.1 M GdnHCl stocks in 50 mM Tris pH 7.5, 1 mM DTT, added to give a final volume of 225 µl, and 11.1 µM protein. For rapamycin binding the 0 and 4.1 M GdnHCl stock solutions both contained 22.5 µM rapamycin (from a 54 mM stock in EtOH), giving a 20 µM final concentration.

Figure 12A:
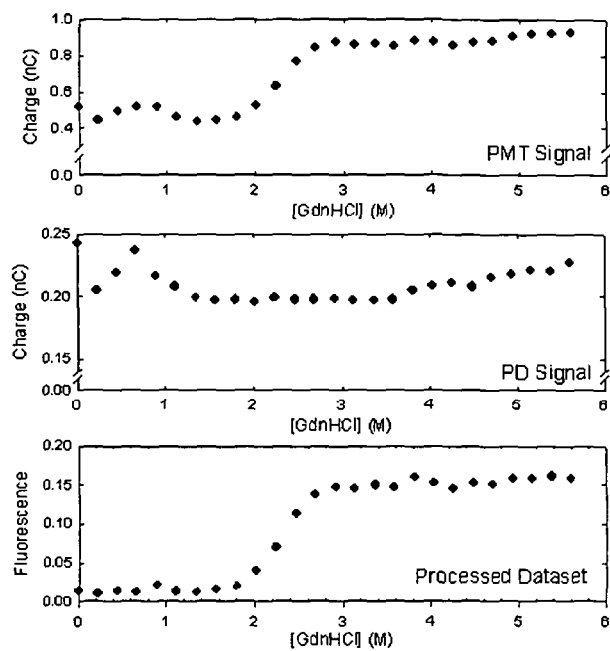
FIG. 12 shows fluorescence measurements of FKBP-12 denaturation at equilibrium.
Figure 12B:
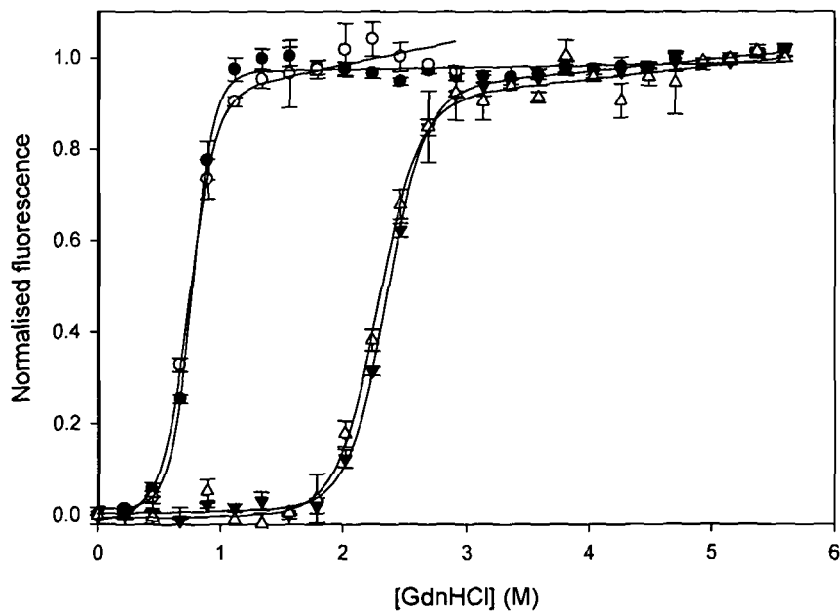

The denaturation curves for wild-type FKBP-12 were compared directly in FIG. 12 and show very good agreement between those measured in microplates and those made using the capillary-based technique. FIG. 12A provides the raw data obtained for a single replicate as fluorescence emission at the photomultiplier tube (PMT) and excitation laser intensity at the photodiode (PD) for a typical denaturation curve acquisition. The final fluorescence measurement (labelled "processed dataset") was obtained as the ratio of the PMT to the PD signals, to account for time-dependent variations of the incident laser source between measurements, with a similar ratio for the blank subtracted. These data are then normalised to unity for high [GdnHCl] to produce the curves shown in panel b. FIG. 12B shows the effect of rapamycin on the equilibrium denaturation of 10 µM wild-type FKBP by guanidine HCl in the presence (triangles) and absence (circles) of 15 µM rapamycin, as measured by the change in the normalised intrinsic fluorescence intensity of samples in 50 mM Tris.HCl, pH 7.5, 24° C. in a capillary (open symbols) and in a 96-well microplate (closed symbols). Error bars shown are standard deviations from triplicate measurements. The best fits to equation below are also shown for each dataset.

$$F_{obs} = \frac{(F_N^0 + m_N[D]) + e^{\left(\frac{m_G[D-C_{1/2}]}{RT}\right)}(F_U^0 + m_U[D])}{e^{\left(\frac{m_G[D-C_{1/2}]}{RT}\right)} + 1}$$

Figure 13:
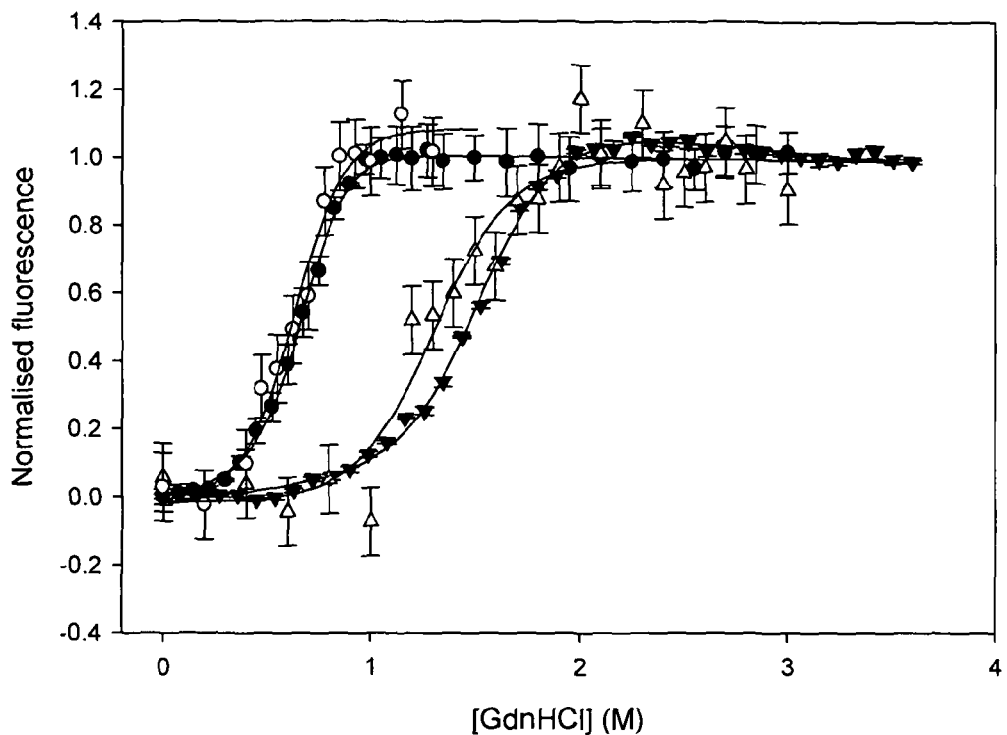
FIG. 13 shows the effect of rapamycin on the equilibrium denaturation of FKBP F99L by guanidine hydrochloride.

As with FIG. 11A above, the raw data in FIG. 12A demonstrates the need for continuously monitoring the incident laser intensity with a photodiode and also illustrates the good signal-to-noise ratio obtained. The curves for the F99L mutant are also compared in FIG. 13. The denaturation curves are shown in the presence (triangles) and absence (circles) of 20 µM rapamycin, as measured by the change in normalised intrinsic fluorescence intensity of samples in 50 mM Tris.HCl, pH 7.5, 22° C. in a capillary at 2 µM FKBP F99L (open symbols) and in a 96-well microplate at 10 µM FKBP F99L (closed symbols). The sharp sigmoidal transition, expected for cooperative two-state unfolding, was observed in all cases. Table 2 (above) and Table 3 (below) display the thermodynamic parameters obtained from each curve and also compare them to known values from the literature.

TABLE 3

Rapamycin dissociation constants for FKBP-12 wt and FKBP-12 F99L

| Protein | $\Delta\Delta G_{binding}$ (kcal mol$^{-1}$)[a] | | | $K_d$ (nM) | | |
|---|---|---|---|---|---|---|
| | Capillary[b] | Microplate[b] | Capillary | Microplate | Literature |
| FKBP-12 wt | 3.86 ± 0.6 | 3.54 ± 0.5 | 7.4 ± 4.7 | 12.8 ± 6.8 | 0.2[c], 0.27[d], 0.35[e], 99.6[f] |
| FKBP-12 F99L | 1.15 ± 0.4 | 1.13 ± 0.4 | 1760 ± 810 | 1850 ± 780 | Not Available |

[a] $\Delta\Delta G_{binding}$ and errors were determined from $\Delta G_{<mG>}$ and associated error values in Table 2.
[b] Capillary and microplate measurements were obtained with 10 µM FKBP-12 wt or 11.1 µM FL99 FKBP-12, in 15 or 20 µM rapamycin, 50 mM Tris.HCl at pH 7.5, 1 mM DTT, 25° C. Literature values were obtained by a range of techniques and conditions
[c] Radiolabeled competition assay with 1 nM FKBP, 0.3-10 nM rapamycin in 100 mM NaCl, 20 mM phosphate, 1 mM EDTA, pH 7.3, 0.015% Triton X-100 (Bierer, B. E. et al. Two distinct signal transmission pathways in T lymphocytes are inhibited by complexes formed between an immunophilin and either FK506 or rapamycin. *Proc. Natl. Acad. Sci. U.S.A* 87, 9231-9235 (1990))
[d] Surface Plasmon Resonance (SPR) with GST-FKBP fusion in PBS pH 7.4, 0.02% Tween-20, 50 nM rapamycin (Banaszynski, L. A., Liu, C. W., & Wandless, T. J. Characterization of the FKBP.rapamycin.FRB ternary complex. *J. Am. Chem. Soc.* 127, 4715-4721 (2005))
[e] Fluorescence polarization competition assay with a fluorescein-labelled synthetic ligand, 5 nM FKBP, 0.05-100 nM rapamycin, PBS pH 7.4, 0.011% Triton X-100, 0.1 mg/ml bovine γ-globulin (Banaszynski, L. A., Liu, C. W., & Wandless, T. J. Characterization of the FKBP.rapamycin.FRB ternary complex. *J. Am. Chem. Soc.* 127, 4715-4721 (2005))
[f] Calculated from available intrinsic protein fluorescence equilibrium denaturation data using a 900 µL sample of 2 µM FKBP-12, 20 µM rapamycin, 50 mM Tris.HCl at pH 7.5, 1 mM DTT, 25° C. (Main, E. R. & Jackson, S. E. Does trifluoroethanol affect folding pathways and can it be used as a probe of structure in transition states? *Nat. Struct. Biol.* 6, 831-835 (1999))

As expected, the stability of both the wild-type FKBP-12 and the mutant F99L increase in the presence of rapamycin. For wild-type the unfolding free energy increases by between 3 and 4 kcal mol$^{-1}$, whereas for F99L an increase of only 1.15 kcal mol$^{-1}$ is observed indicating that the mutation affects the binding affinity of the rapamycin. The stability of the native protein is also decreased by 0.92 kcal mol$^{-1}$ upon mutation to F99L which is in close agreement with the 1.2±0.11 kcal mol$^{-1}$ destabilisation observed previously in a standard fluorometer (Main, E.R.G. Thesis: Studies on the immunosuppressant binding protein FKBP12 and the nuclear/steroid receptors vitamin D3 and oestrogen. 2000. University of Cambridge). The transition midpoints also show very good agreement at all scales of measurement and show only a slight decrease in precision from 0.005, to 0.01 and 0.02 M GdnHCl for wild type at the respectively smaller scales.

Further, photobleaching in the capillary does not occur at the flow rates used as the sample can only be excited once given the 200 μm laser spot and 1 kHz laser pulsing.

Figure 14A:
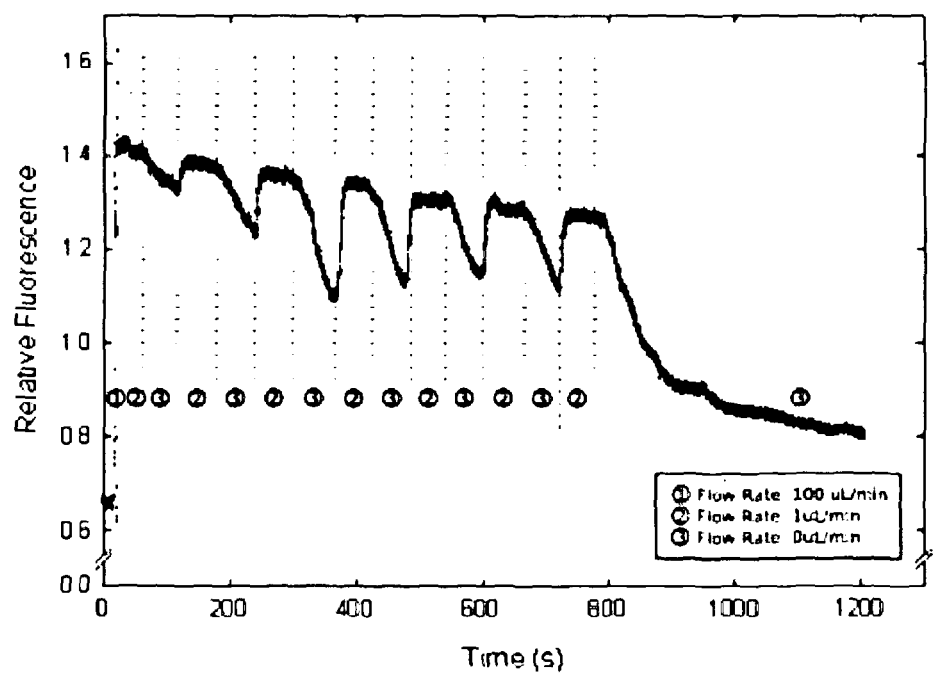
FIGS. 14A and 14B show the effect of low and zero flow rates on the photobleaching of protein samples in the device of the invention.
Figure 14B:
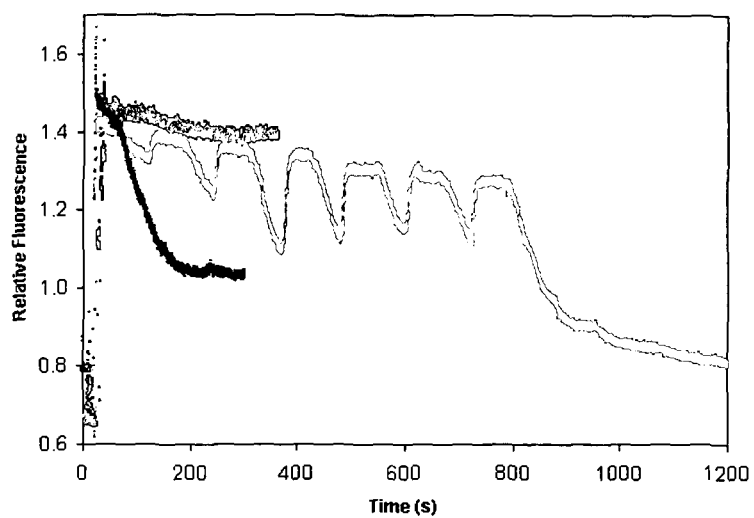

Photobleaching was only observed at flow rates up to 1 μLmin$^{-1}$. This is shown in FIGS. 14A and 14B which illustrate the effect of low and zero flow rates on the photobleaching of protein samples in the capillary. FIG. 14A depicts the oscillation of flow rate between 1 μL/min and 0 μL/min. FIG. 14B is an overlay of measurements at 0 μL/min (black) and 1 μL/min (grey) with the signal from the oscillating flow rate shown in A (light grey).

The photobleaching experiments were completed using a solution of 7.14 μM BSA in 1 M urea and 50 mM Tris.HCl, pH 7.2 which was passed through the capillary. Initially a flow rate of 100 μL/min was used to flush the capillary and then a repeating cycle of 1 μL/min then 0 μL/min (flow stopped) was performed. As seen in FIG. 14A, initially the signal was stable at 100 μL/min. When the flow was stopped the fluorescence signal immediately began to decay, indicating photobleaching of the protein and loss of fluorescence. Flow at 1 μL/min also showed photobleaching but gave a much slower rate of signal loss than at 0 μL/min. The signal continued to decrease at 1 μL/min even though the sample within the measurement zone of the capillary was replaced many times. This indicated a gradual deposition of the photobleached protein on the capillary surface over time. In all experiments reported the flow-rate was set to at least 10 μL/min for which no photobleaching was observed in any protein signals.

Ligand dissociation constants were obtained by measuring the free-energy of denaturation for native proteins in the presence and absence of the ligand (Tang, L. et al. H/D exchange- and mass spectrometry-based strategy for the thermodynamic analysis of protein-ligand binding. *Anal. Chem.* 79, 5869-5877 (2007)). The dissociation constants for rapamycin binding to both wild-type and F99L FKBP-12 derived using the inventive technique, were compared to values obtained by other methods, the results are shown in Table 3. For wild-type FKBP-12, literature values vary in the range 0.2-99.6 nM from various techniques, samples and solution conditions. The microplate-based fluorescence technique gave a value of 12.8 nM, and the inventive technique gave 7.4 nM, both consistent with the existing literature data. This demonstrates that the capillary technique can obtain useful dissociation constant measurements using significantly reduced quantities of sample.

The dissociation constant obtained for rapamycin and the F99L mutant of FKBP-12 was determined to be 1.8 μM using the inventive technique, showing a 240-fold loss of affinity relative to wild-type. The intermolecular coupling energy between rapamycin and the mutated phenylalanine residue in FKBP-12 was also calculated from the free-energies determined in the capillary by using a double-mutant cycle analysis (Carter, P. J., Winter, G., Wilkinson, A. J., & Fersht, A. R. The use of double mutants to detect structural changes in the active site of the tyrosyl-tRNA synthetase (*Bacillus stearothermophilus*). *Cell* 38, 835-840 (1984)). This interaction energy was found to be 3.0±1.3 kcal mol$^{-1}$, which is a significant proportion of the total interaction of 4.05 kcal mol$^{-1}$ between FKBP-12 and rapamycin.

Example 3

Thermal Excitation Using an Infra-Red Laser in a Microwell

Figure 15:
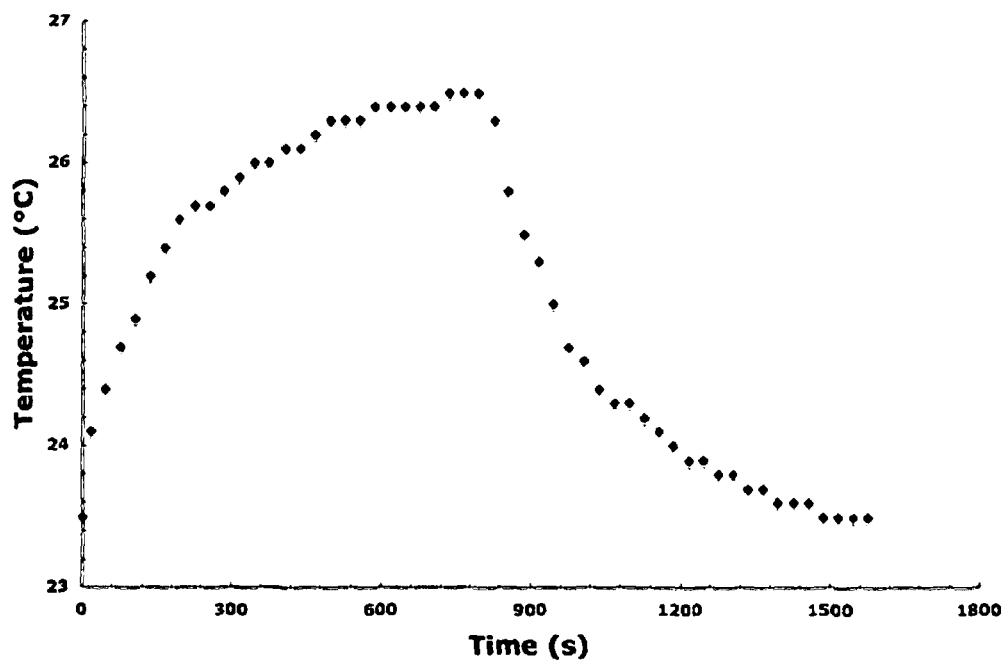
FIG. 15 shows the evolution of the temperature of 75 μL of water in a 384-well plate microwell placed under the radiation of a 10 mW power IR laser.

Initial measurements were taken for the evolution of temperature in a microwell using infra-red excitation to demonstrate the control of temperature using IR radiation, and to predict the temperature control of fluids in a microfluidic channel using an IR laser [G145PU0450M, Roithner]. A volume of 75 μL of water was placed in a standard 384-well microwell illuminated by an IR laser (λlaser=1550 nm, Power laser=10 mW). A thermocouple was placed inside the liquid, close to the side of the microwell to avoid direct interaction of the thermocouple with the IR laser radiation, and was used to measure the temperature of the solution as a function of time as shown in FIG. 15. When the laser was turned on, the temperature was measured every 30 seconds and resulted in an increase of temperature of 3.5 K from 23° C. to 26.5° C. over 800 seconds. At this point in time the laser was turned off, and the temperature then decreased at a similar rate back to room temperature (23° C.). This experiment demonstrated that the IR irradiation of a sample containing water generated an increased sample temperature and provided data with which to model the heating of samples in microfluidic channels using IR irradiation with the same laser.

Example 4

Simulation of the Evolution of Temperature Along an IR Heated Channel

Figure 16:
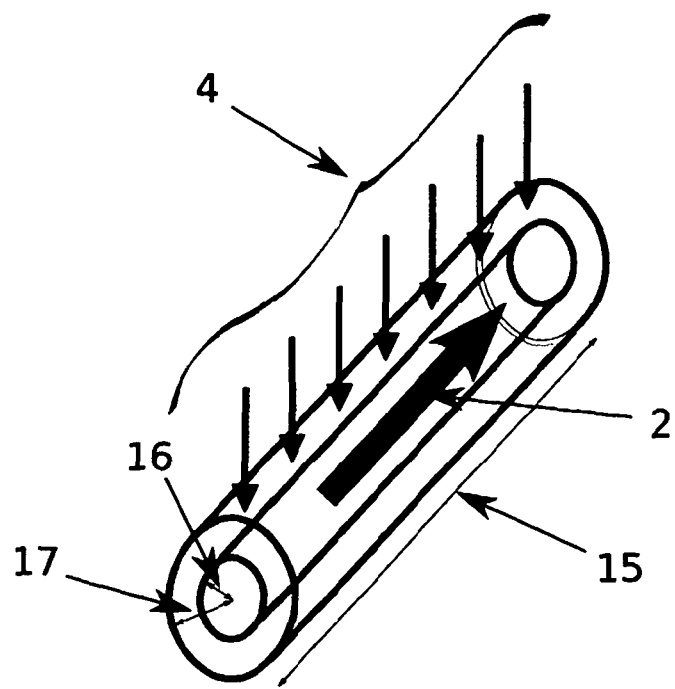
FIG. 16 is a schematic representation of the different characteristics considered for the Labview calculations.

After measuring the temperature rise of a static liquid contained in a microwell using an infra-red radiation source absorbed through a known sample path length, a simulation of the evolution of the temperature along an entire capillary containing water passing along the capillary at a defined flow rate was conducted. The liquid was heated progressively as it flowed along the capillary by simulating an external IR source that brings 1550 nm photons evenly along the capillary, as represented in FIG. 16.

The simulation model is based on a basic thermal dissipation law applied to a pipe with a length $L_{section}$ 15, internal radius $R_{int}$ 16 and external radius $R_{ext}$ 17 with a thermal conduction λ. If the temperature difference ΔT between the inside of the tube and the outside of the tube is considered, during a time t, the thermal dissipation $Q_{out}$ follows this equation:

$$Q_{out} = \frac{2\pi\lambda L_{section}}{\ln\left(\frac{R_{ext}}{R_{int}}\right)} t.\Delta T$$

Figure 17:
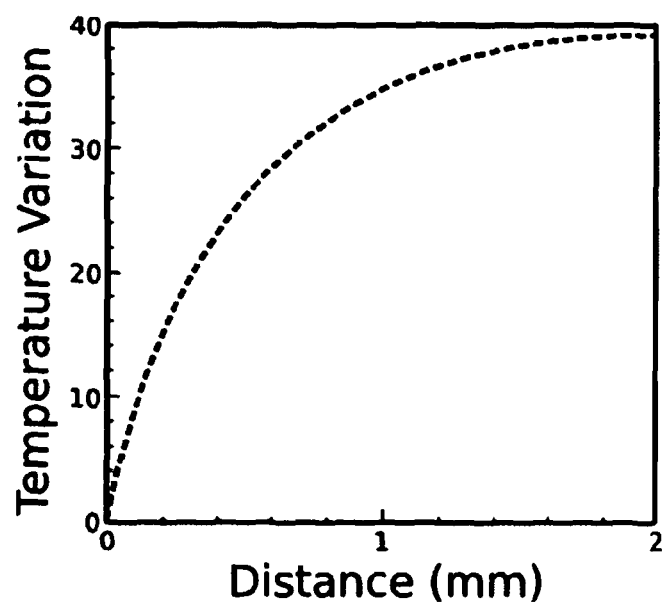
FIG. 17 shows a simulated evolution of the temperature of water flowing at 2 μL/min in a 25 μm internal diameter channel under 1550 nm IR radiation using a source of 24 mW.

Considering the amount of heat entering the system, $Q_{in}$, and exiting the system, $Q_{out}$, for a small section of the entire pipe and then applying an iterative procedure to determine the temperature increase, it is possible to predict the variation of temperature along the length of the channel. The model predictions were calculated using Labview software and gave rise to the simulated temperatures shown in FIG. 17 as a function of distance along the length of the channel defined by the following characteristics:

Heated length: 2 mm
Internal diameter: 25
External diameter: 200
Thermal conduction of PMMA: 0.18 W m$^{-1}$ K$^{-1}$
Flow rate: 2 µL min$^{-1}$
Laser Power: 24 mW The simulation predicts a 39K gradient of the liquid temperature from the beginning to the end of the capillary. This variation is sufficient to obtain complete denaturation curve for most known proteins. The model also enables the variation of temperature along the length of a microfluidic channel to be calibrated.

Example 5

Experimental Thermal Excitation of a Sample in a Capillary

Figure 18:
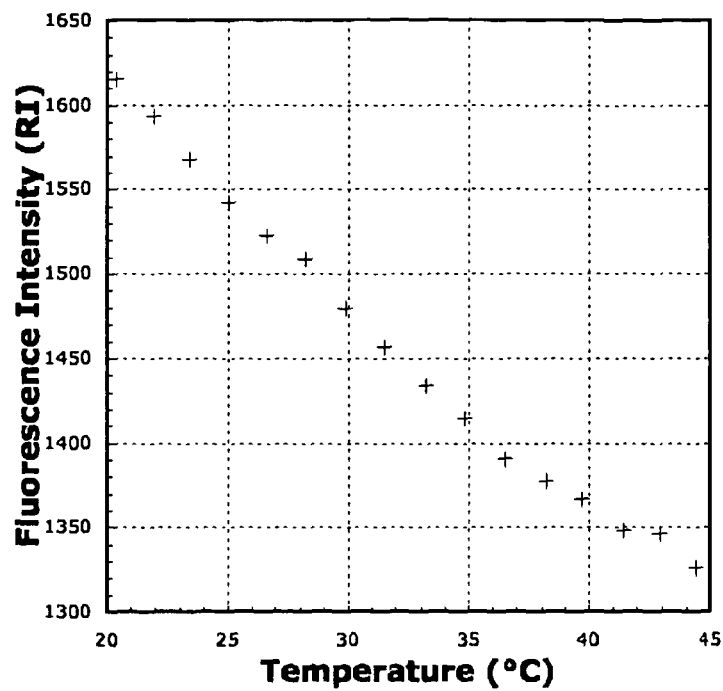
FIG. 18 is a calibration curve for the variation of the fluorescence intensity of 2 mg·ml$^{-1}$ TAMRA in water, as a function of temperature, in a capillary of diameter 100 μm, measured using confocal microscope with excitation wavelength of 543 nm and emission wavelength of 608 nm.

A preliminary experiment to demonstrate thermal excitation of a liquid in a capillary using an infra-red laser is described. The temperature in the channel was determined using the temperature sensitive fluorescent dye TAMRA. The variation of fluorescence intensity as a function of temperature was calibrated at 2 mg·ml$^{-1}$ TAMRA in water as a function of the temperature, in a capillary of diameter 100 µm, measured using confocal microscope with excitation wavelength of 543 nm and emission wavelength of 608 nm as presented in FIG. 18.

Figure 19:
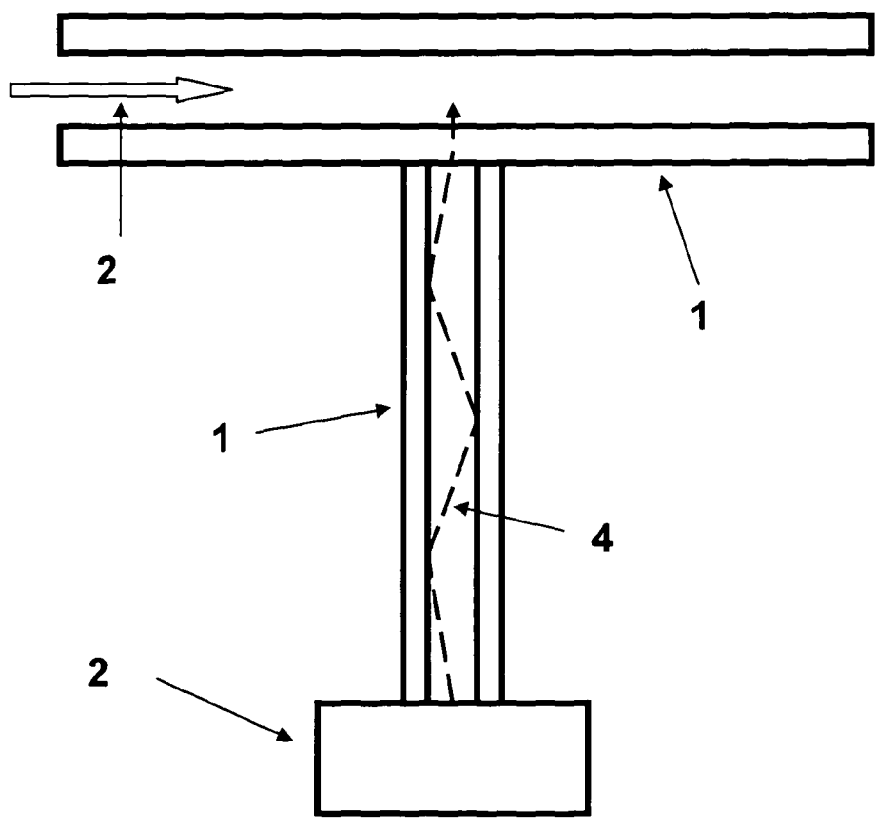
FIG. 19 is a schematic representation of the heating of a sample in a capillary by infra-red radiation carried by an optical fibre that is perpendicular to the side of the capillary.
Figure 20:
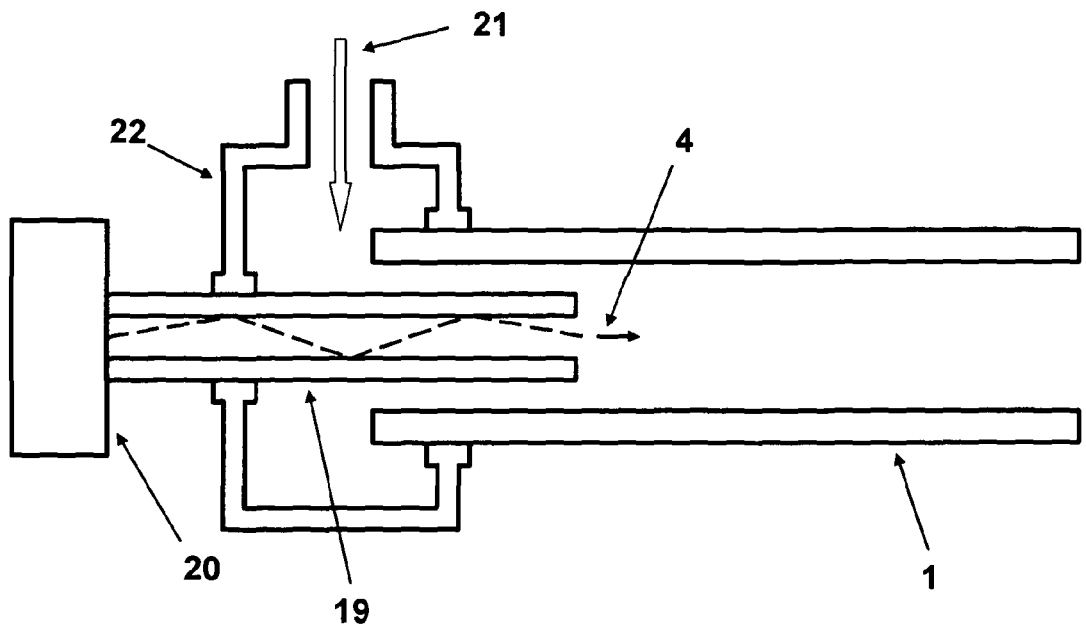
FIG. 20 is a schematic representation of the heating of a sample in a capillary by infra-red radiation carried in an optical fibre that is placed inside the capillary such that the light is passed in parallel with the sample flow.

Two different experiments were carried out using a solution of TAMRA in a capillary, and determining the fluorescence intensity of the TAMRA with a confocal microscope. In the first experiment, the sample was illuminated with infra-red radiation 4 from a laser source 20 via an optical fibre 19 brought to the side of the capillary 1, perpendicular to the sample flow 21 (FIG. 19). This set up would be used such that the infra-red radiation is brought to a sample capillary (or other channel) at one or more sites along its length using optical fibres and/or waveguides. In the second experiment, the optical fibre 19 was passed into the capillary 1 in parallel with the sample flow as in FIG. 20. The sample 21 passed into a water-tight housing 22 and then along the capillary (or other channel).

Optical Fibre Perpendicular to the Capillary

A multimode optical fibre 19 with a 100 µm core was brought in contact perpendicular to a capillary with an internal diameter of 100 µm. The other end of the optical fibre was linked to an IR LaserDiode 20, FU68PDF-5/Fitel/$\lambda_{IR}$=1550 nm/P$_{IR}$=24 mW). A flow 21 of TAMRA was passed into the capillary. The system was then placed under a confocal fluorescence microscope to record the evolution of the fluorescence intensity of the TAMRA (excitation 543 nm, reemission 608 nm). The variation of the intensity around the position of the optical fibre in the capillary was determined and is presented in FIG. 21A. This graph permits to consider a local variation of temperature of about 12° C. generated by the IR radiation in the water.

The experiment was repeated with significantly improved alignment of the IR light source with the capillary using the device in FIG. 2B. FIG. 21B shows the results obtained using the device of FIG. 2B. Specifically, FIG. 21B shows the temperature gradient obtained over a range of flow rates. It can be seen that by controlling the flow rate of the sample through the capillary, the temperature of the sample can be precisely controlled.

Optical Fibre Passed Inside the Capillary

Using a watertight T-Junction (22,P-890/Upchurch scientific), the optical fibre was placed 19 directly inside a capillary 1 of 250 µm internal diameter (FS, deactivated-0.250 mm/Agilent). The optical fibre was linked to a more powerful laser diode (FOL1425R/FITEL/$\lambda_{IR}$=1450 nm/P$_{IR}$=400 mW). A flow of TAMRA of 100 µl/min was set up in the capillary. The intensity of the TAMRA fluorescence is shown in FIG. 22 as measured under a confocal microscope as previously. FIG. 22 shows a view of the median plane of the optical fibre and the 2D cartography of the temperature in front of the optical fibre 19. A variation of intensity of 700 RI corresponding at a temperature variation of 60° C. is observed in the capillary. At this flow rate, a gradient increase of 60° C. in the sample along the length of the capillary, is achieved within 12 ms.

Example 6

Construction of a Microfluidic Chip with Integrated Thermal Excitation by Infra-Red and Detection of the Intrinsic Fluorescence of Protein Samples The waveguide structure on the chip is composed of alternating air gaps and polymer lines which creates two types of waveguides in parallel, where both types are placed on either side of the channel. On one side of the channel, the waveguides are used to bring the UV 266 nm excitation and IR 1550 nm for heating, and the other side transmits the fluorescence emission signal (e.g. UV 340 nm) to the detector.

The radiation sources can be transmitted to the waveguides that direct them to side of the channel, by using an optical fibre composed of fused silica. Fused silica has a very low absorption coefficient in the UV ($\alpha_{266\ nm}$=5.5×10$^{-5}$ cm$^{-1}$) and the IR ($\alpha_{1550\ nm}$=10$^{-4}$ cm$^{-1}$) corresponding to a loss of power of 1.09% in the UV and 1.98% in the IR for a fibre of one meter in length. The coupling of two optical fibres by existing methods known to those skilled in the art can be used to create a single optical fibre carrying both the UV and IR radiation sources. This optical fibre can then be similarly split into 32 radiation transmitting fibres, each transmitting the two wavelengths to an array of 32 parallel waveguides at positions placed adjacently along the length of the channel. The efficient localization of those 32 channels is enabled using a waveguide fabricated by the anisotropic etching of a substrate of silicon following the crystalline planes (Steinsland, Sens. Act. 86 (2000) 73-80).

An identical or similar waveguide design is fabricated on the opposite face of the microfluidic channel such that the two opposing waveguides are aligned along the channel length. Each optical fibre used for bringing the incident radiation sources or for detecting the emission signal, is aligned with the edge of the microfluidic chip and with the waveguides. In one design (FIG. 3A), open space optical waveguides are selectively etched at the surface of the chip. The air composing the core 8 of the waveguide has no absorption at most UV and IR wavelengths. The cladding 9 is shaped in the layer of polymer to create the walls of the channel and the UV 340 nm transmitting waveguides.

After travelling all along the waveguide 8, the photons arrive at the wall of the channel (thickness=50 microns) and cross this wall to enter the channel. On the other side of the channel a polymer waveguide 9 (e.g. of length 5 mm) is placed to collect the emitted signal from protein fluorescence e.g. at 340 nm. The transmittance of this material can be 95% for both UV (340 nm) and IR (1550 nm) such as with CYTOP (Asahi Glass Co. (AGC)). The 32 optical fibres collecting the photons on the opposite face of the device bring the photons onto a UV sensitive CCD array. The signal obtained with the CCD is analysed and permits the observation of the fluorescence of the protein at each of the 32 points along the microfluidic channel. Simultaneous infrared heating of the sample also at each of the 32 points along the microfluidic channel creates a temperature gradient such that each of the 32 fluorescence measurements is of the same sample but at different temperatures such that for example a complete thermal denaturation profile for a protein can be obtained simultaneously.

The fluidic junction of the chip with the outside is permitted thanks to a soft layer 23 placed between the chip and the motherboard. This layer is composed of a silica gel, the PDMS, material that can easily be moulded in a Teflon master.

Example 7

Supporting Calculations and Experiments

Determination of Thermodynamic Parameters

Two-state protein denaturation was assumed, as previously observed for FKBP-12 (Main, E. R. & Jackson, S. E. Does trifluoroethanol affect folding pathways and can it be used as a probe of structure in transition states? *Nat. Struct. Biol.* 6, 831-835 (1999)). Data for the observed fluorescence ($F_{obs}$) as a function of denaturant concentration ([D]) were fit using SigmaPlot 10.0 (Systat Software, Hounslow, UK) to the equation below:

$$F_{obs} = \frac{(F_N^0 + m_N[D]) + e^{\left(\frac{m_G[D-C_{1/2}]}{RT}\right)}(F_U^0 + m_U[D])}{e^{\left(\frac{m_G[D-C_{1/2}]}{RT}\right)} + 1}$$

This allowed the calculation of $m_G$, $C_{1/2}$, $F^0_N$, $F^0_U$, $m_N$ and $m_U$ with errors (Pace, C. N. Determination and analysis of urea and guanidine hydrochloride denaturation curves. *Methods Enzymol.* 131, 266-280 (1986)), where R is the gas constant (1.987 cal $K^{-1}$ $mol^{-1}$), T is 298 K, $C_{1/2}$ (M) is the denaturant concentration at which 50% of the protein is denatured, $F^0_N$ and $F^0_U$ are the respective fluorescence signals of the native and unfolded states at 0 M denaturant, $m_G$ (kcal $mol^{-1}$ $M^{-1}$) is the slope (dG/d[D]) of the free energy of unfolding as a function of denaturant concentration, $m_N$ is the slope ($dF_N$/d[D]) for the native state baseline, and $m_U$ the corresponding parameter for the unfolded state. The free energy of protein denaturation in water $\Delta G_{H2O}$ was calculated as $m_G C_{1/2}$, using the fitted $m_G$, where we set the denaturant dependent free energy ($\Delta G_{obs}$) to zero in the equation below when [D] is equal to $C_{1/2}$.

$$\Delta G_{obs} = \Delta G_{H2O} + m_G[D]$$

Values of $\Delta G_{H2O}$ were used to calculate the change in free energy of the mutant or ligand bound protein, $\Delta\Delta G_{X-WT}$, relative to un-liganded wild-type FKBP-12. The change in free energy of unfolding upon ligand binding, $\Delta\Delta G_{binding}$, was calculated for each mutant from the values of $\Delta G_{H2O}$ for liganded FKBP-12 relative to $\Delta G_{H2O}$ for non-liganded FKBP-12. At saturating total ligand $[L_{TOT}] \gg [P_{TOT}]$, where $[P_{TOT}]$ is the total protein concentration, the dissociation constant $K_d$ for binding to protein can be deduced from the equation below and $\Delta\Delta G_{binding}$ (Tang, L. et al. H/D exchange- and mass spectrometry-based strategy for the thermodynamic analysis of protein-ligand binding. *Anal. Chem.* 79, 5869-5877 (2007)), assuming the free ligand concentration $[L] \approx [L_{TOT}]$.

$$K_d = \frac{[L_{TOT}]}{\exp\left(-\frac{\Delta\Delta G_{binding}}{RT}\right) - 1}$$

Under non-saturating conditions the free ligand [L] and protein [P] concentrations must first be determined from $[L_{TOT}]$ and $[P_{TOT}]$ (see Supplementary Information online) giving the following equation to determine the $K_d$.

$$K_d = \frac{\left(\frac{[L_{TOT}]}{\exp\left(-\frac{\Delta\Delta G_{binding}}{RT}\right) - 1}\right) + 1[L_{TOT}] - [P_{TOT}]}{\exp\left(-\frac{\Delta\Delta G_{binding}}{RT}\right)}$$

Errors in $K_d$ are mainly from $m_G$ values obtained by curve fitting to:

$$F_{obs} = \frac{(F_N^0 + m_N[D]) + e^{\left(\frac{m_G[D-C_{1/2}]}{RT}\right)}(F_U^0 + m_U[D])}{e^{\left(\frac{m_G[D-C_{1/2}]}{RT}\right)} + 1}$$

As we do not expect this parameter to vary between mutants of FKBP-12 (our measurements are consistent with this assumption), we have used the values $<m_G>$, averaged over the two variants, to calculate for both liganded and un-liganded proteins, more accurate ($\Delta G_{<mG>}$) values for $\Delta G_{H2O}$.

Viscosity of the BSA (Bovine Serum Albumin) Solution

The solution used to test the device is a BSA+water solution at various concentrations. The viscosity of the solution was studied as a function of BSA concentration by using a cylinder rheometer Instron 1140, as shown in FIG. 23. The exponential change of the viscosity of BSA solutions with increasing BSA concentration allowed the determination of the range of sample viscosities that are able to be passed through a channel of defined size and cross-sectional shape, without increasing the pressure within the system beyond the maximum likely to result in leakage of the sample or damage to the fluidics system.

Pressure Considerations

Consider a cylindrical pipe with a length L and an inside radius R in which pass a liquid with a viscosity v at a flow rate f. The Poiseuille equation links these parameters with the pressure gradient between the ends of the pipe as follows:

$$\Delta P = \frac{8 v f L}{\pi R^4}$$

A study concerning the generalization of Poiseuille's law to any channel is available (Mortensen, *Phys. Rev.* E74, 017301 (2006) and follows the following equation:

$$\Delta P = \frac{28.48 vfL}{a^4}$$

for a square channel with the square sides of length "a".

This equation and the concentration considerations presented above allows the calculation of the pressure in the channel with BSA solutions of a certain protein concentration and a defined sample flow rate.

The examples above show that it is possible to measure the properties of a sample using the device of the invention. Thermodynamic parameters may then be derived using known techniques. As such, the invention provides a method to determine parameters such as dissociation constants or denaturing constants using signals obtained from the sample using small sample volumes, low concentrations and high through puts, thereby avoiding any risk that photobleaching may occur. It has been shown that the inventive devices can heat rapidly and that the local temperature within the sample cavity can be controlled.

It should be appreciated that the devices and methods of the invention are capable of being incorporated in the form of a variety of embodiments, only a few of which have been illustrated and described above.

The invention claimed is:

1. A microfluidic device, for analysis, comprising:
a chip comprising a channel having a cross sectional area with a width less than or equal to 150 μm and a depth less than or equal to 150 μm;
a first source of radiation comprising a light emitting diode or a laser which emits electromagnetic radiation having a wavelength of 1400 nm to 1600 nm for directly heating a sample placed in the channel in use; and
an analytical assembly configured to record a change in the sample arising from heating of the sample with the first source of electromagnetic radiation;
wherein the first source of electromagnetic radiation comprises multiple sources of electromagnetic radiation or a single source of electromagnetic radiation arranged so that the electromagnetic radiation is directed along the length of the channel, such that the sample is heated uniformly across the cross-sectional area of the channel and along the length of the channel.

2. The device according to claim 1, wherein each of the multiple sources of the first source of electromagnetic radiation is directed at a different region of the sample in the channel.

3. The device according to claim 1, wherein each of the multiple sources of the first source of electromagnetic radiation emits electromagnetic radiation at a different frequency.

4. The device according to claim 1, wherein the analytical assembly comprises a detector and a second source of electromagnetic radiation, wherein the second source of electromagnetic radiation interacts with the sample to produce a signal measurable by the detector.

5. The device according to claim 4, wherein the second source of electromagnetic radiation comprises multiple sources of radiation each emitting electromagnetic radiation at the same frequency.

6. The device according to claim 5, wherein the multiple sources of the first source of electromagnetic radiation and/or the multiple sources of the second source of electromagnetic radiation are arranged so that the electromagnetic radiation meets a wall of the channel at an angle in the range 30°-150° relative to the longitudinal axis of the channel.

7. The device according to claim 1, configured for use with a static or a flowing sample.

8. The device according to claim 7, wherein the flow rate for a flowing sample is in the range 0.5-5 μl min$^{-1}$.

9. The device according to claim 1, wherein the first source of electromagnetic radiation emits electromagnetic radiation selected from visible and infra-red radiation.

10. A process for the detection of a signal, comprising placing a sample into a microfluidic device of claim 1; and recording a change in the sample as a result of a heating process.

11. The process according to claim 10, wherein the sample comprises solution plugs in a cavity which is a channel or a single sample flowing through the channel.

12. The process according to claim 10, wherein a property selected from a thermal gradient, an amplitude of a thermal gradient in the sample, and an absolute temperature in the sample; is modulated by altering the flow rate of the sample through the channel in a flowing sample, or by altering the power of the first source of electromagnetic radiation in a flowing or a static sample.

13. The process according to claim 10, wherein a shape of a thermal gradient in the sample is modulated by altering the power of one or more of multiple first sources of electromagnetic radiation positioned adjacent to different points of the channel.

14. The process according to claim 10, wherein the sample is alternately heated and cooled by altering the power of the first source of electromagnetic radiation applied to the sample.

15. The process according to claim 10, wherein the sample comprises a protein and the change in the sample as a result of the heating process is protein denaturation.

* * * * *